(12) United States Patent
Keating et al.

(10) Patent No.: US 7,125,837 B1
(45) Date of Patent: Oct. 24, 2006

(54) ELASTIN-BASED COMPOSITIONS

(75) Inventors: Mark T. Keating, Chestnut Hill, MA (US); Dean Y. Li, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/554,996

(22) PCT Filed: Feb. 28, 2000

(86) PCT No.: PCT/US00/02526

§ 371 (c)(1),
(2), (4) Date: May 24, 2001

(87) PCT Pub. No.: WO00/50068

PCT Pub. Date: Aug. 31, 2000

Related U.S. Application Data

(63) Continuation-in-part of application No. 09/258,217, filed on Feb. 26, 1999, now Pat. No. 6,903,244.

(51) Int. Cl.
| | |
|---|---|
| A01N 37/18 | (2006.01) |
| A61K 38/00 | (2006.01) |
| A61K 39/00 | (2006.01) |
| C07K 1/00 | (2006.01) |
| A61F 2/06 | (2006.01) |

(52) U.S. Cl. .................. 514/2; 530/300; 530/350; 424/185.1; 623/1.11

(58) Field of Classification Search .............. 514/2; 530/300, 350; 435/287.1; 424/185.1; 623/1.11
See application file for complete search history.

(56) References Cited

U.S. PATENT DOCUMENTS

| | | | |
|---|---|---|---|
| 4,323,358 A | 4/1982 | Lentz et al. ............. 8/94.11 |
| 4,352,887 A | 10/1982 | Reid et al. .............. 435/240 |
| 4,553,974 A | 11/1985 | Dewanjee ............... 8/94.11 |
| 4,739,762 A | 4/1988 | Palmaz .................. 128/343 |
| 4,877,599 A | 10/1989 | Lees ....................... 424/1.1 |
| 4,960,423 A | 10/1990 | Smith ..................... 623/1 |
| 4,976,734 A | 12/1990 | Urry et al. .............. 623/11 |
| 5,064,430 A | 11/1991 | Urry ...................... 623/1 |
| 5,336,256 A | 8/1994 | Urry ...................... 623/1 |
| 5,591,224 A | 1/1997 | Schwartz et al. ........ 623/1 |
| 5,595,571 A | 1/1997 | Jaffe et al. ............... 8/94.11 |
| 5,628,785 A | 5/1997 | Schwartz et al. ........ 623/1 |
| 5,650,282 A | 7/1997 | Keating et al. ........... 435/6 |
| 5,716,394 A | 2/1998 | Bruchman et al. ...... 623/1 |
| 5,720,777 A | 2/1998 | Jaffe et al. .............. 623/2 |
| 5,726,153 A | 3/1998 | Lees et al. ............... 514/12 |
| 5,728,420 A | 3/1998 | Keogh ................... 427/2.12 |
| 5,749,895 A | 5/1998 | Sawyer et al. .......... 606/214 |
| 5,776,182 A | 7/1998 | Bruchman et al. ...... 623/1 |
| 5,791,352 A | 8/1998 | Reich et al. ............ 128/898 |
| 5,840,489 A | 11/1998 | Keating et al. ........... 435/6 |
| 5,843,180 A | 12/1998 | Jaffe et al. ............... 623/2 |
| 5,843,181 A | 12/1998 | Jaffe et al. ............... 623/2 |
| 5,852,009 A | 12/1998 | Cerami et al. .......... 514/212 |
| 5,855,620 A | 1/1999 | Bishopric et al. ....... 623/11 |
| 5,856,245 A | 1/1999 | Caldwell et al. ........ 442/76 |
| 5,858,662 A | 1/1999 | Keating et al. ........... 435/6 |
| 5,874,164 A | 2/1999 | Caldwell ................ 428/306.6 |
| 5,891,506 A | 4/1999 | Keogh ................... 427/2.13 |
| 5,891,558 A | 4/1999 | Bell et al. ............... 428/218 |
| 5,925,552 A | 7/1999 | Keogh et al. ........... 435/174 |
| 5,928,916 A | 7/1999 | Keogh ................... 435/174 |
| 5,945,319 A | 8/1999 | Keogh ................... 435/174 |
| 5,955,055 A | 9/1999 | Lees et al. .............. 424/1.69 |
| 5,969,106 A * | 10/1999 | Rothstein et al. ........ 530/353 |
| 5,972,890 A | 10/1999 | Lees et al. .............. 514/13 |
| 5,990,379 A | 11/1999 | Gregory ................ 623/11 |

FOREIGN PATENT DOCUMENTS

| | | |
|---|---|---|
| JP | 59112909 | 6/1984 |
| JP | 59112951 | 6/1984 |
| WO | WO 90/07936 | 7/1990 |
| WO | WO 92/19195 | 11/1992 |
| WO | WO 92/22309 | 12/1992 |
| WO | WO 94/25503 | 11/1994 |
| WO | WO 95/01203 | 1/1995 |
| WO | WO 95/05452 | 2/1995 |
| WO | WO 96/02286 | 2/1996 |
| WO | WO 96/02646 | 2/1996 |

(Continued)

OTHER PUBLICATIONS

Fazio et al., Isolation and Charaterization of Human Elastin cDNAs, and Age-Associated Varation in Elastin Gene Expression in Cultured Skin Fibroblast, 1988, Laboratory Investigation, vol. 58, No. 3, pp. 270-277.*

(Continued)

*Primary Examiner*—Shin-Lin Chen
(74) *Attorney, Agent, or Firm*—Fish & Neave IP Group Ropes & Gray LLP

(57) ABSTRACT

The present invention provides screening methods that use organisms or cells that lack function in one or both elastin genes. These methods are useful in identifying drugs for the prevention and treatment of obstructive vascular diseases, such as atherosclerosis, vascular restenosis and transplant arteriopathy. Further, the invention provides pharmaceutical compositions containing elastin-based compositions that are particularly potent regulators of proliferation, differentiation, and migration of smooth muscle cells in vitro and in vivo. These pharmaceutical compositions and related methods are useful in the prevention and treatment of disorders characterized by diminished capacity to regulate smooth muscle cell function.

35 Claims, 12 Drawing Sheets
(7 of 12 Drawing Sheet(s) Filed in Color)

FOREIGN PATENT DOCUMENTS

| WO | WO 96/40871 | | 12/1996 |
|---|---|---|---|
| WO | WO 96/40959 | | 12/1996 |
| WO | WO 97/12635 | | 4/1997 |
| WO | WO 97/34998 | | 9/1997 |
| WO | WO 98/01740 | | 1/1998 |
| WO | WO 98/05685 | * | 2/1998 |
| WO | WO 99/03886 | * | 1/1999 |
| WO | WO 99/45941 | | 9/1999 |
| WO | WO 99/53943 | | 10/1999 |

OTHER PUBLICATIONS

Raju et al., Primary Structures of Bovine Elastin a, b, and c Deducded from the Sequence of cDNA Clones, 1987, The Journal of Biological Chemistry, vol. 262, No. 12, pp. 5755-5762.*
Raju et.al.; Primary Structures of Bovine Elastin a,b and c Deduced from the Sequences of cDNA Clones, 1987, Journal of Biological Chemistry, vol. 262: 5755-5762.*
Skolnick et.al.; From genes to protein structure and function: novel applications of computational approaches in the genomic era, 2000, TIBECH, vol. 18: 34-39.*
Kaye et.al.; A single aminio acid substitution resulds in a retinoblastoma protein defective in phosphorylation and oncoprotein binding, 1990, Proc. Natl. Acad. Sci., vol. 87: 6922-6926.*
Rudinger; Characteristics of the amino acids as components of a peptide hormone sequence, 1976, Peptide Hormones: 1-7.*
Tajima et al., 1997, Archives of Dermatological Research, vol. 289, No. 8, p. 489-492.*
Eck et al., 1996 (Goodman & Gilman's The Pharmacological Basis of Therapeutics, McGraw-Hill, New York, p. 77-101, IDS.*
Adams, J.C. et al., Development 117:1183-1198 (1993).
American Heart Association, Heart and Stroke Facts: 1996 Statistical Supplement(American Heart Association, Dallas, TX) (1996).
Beck, L. and D'Amore, FASEB J. 11:365-373 (1997).
Bloom W. and Fawcett, D., A Textbook of Histology, 10 Ed., pp. 398-402 (Saunders, Philadelphia)(1975).
Boyle, W.A. and Maher G.M., Anesthesiology 82:221-235 (1995).
Burn, J. and Goodship, J. et al., "Developmental Genetics of the Heart" Curr. Opin. Dev. 6:3:322-325 (Jun. 1996).
Carmeliet, P. et al., Nature 380:435-439 (1996).
Cowan, K. et al., "Serine Elastase and Matrix Metalloproteinase (MMP) Inhibition Induced Pulmonary Artery (PA) Smooth Muscle Cell (SMC) Apoptosis Leading to Regression of Vascular Hypertrophy" Molecular Biology of the Cell 8 (Supp.) p. 287A (1997).
Curran, M. et al., Cell 73:159-168 (1993).
Davis, E.C., Lab. Invest. 68:89-99 (1993).
Davis, E.C., J. Histochem. Cytochem. 43:1115-1123 (1995).
Deng, C. et al., Mol. Cell. Biol. 13:2134-2140 (1993).
Dietz, H.C. and Pyeritz, R.E., Hum. Mol. Genet. 4:1799-1809 (1995).
Ewart, A. et al., Proc. Natl. Acad. Sci. USA 90:3226-3230 (1993).
Ewart, A. et al., Nature Genetics 5:11-16 (1993).
Ewart, A. et al., J. Clin. Invest. 93:1071-1077 (1994).
Ferrara, N. et al., Nature 380:439-442 (1996).
Folkman, J. and D'Amore, Cell 87:1153-1155 (1996).
Fong, G.H. et al., Nature 376:66-70 (1995).
Galis, Z.S. et al., J. Clin. Invest. 94:2493-2503 (1994).
Gardner, H. et al., Dev. Biol. 175:301-313 (1996).
George, E.L. et al., Development 119:1079-1091 (1993).
Gibbons, G.H. and Dzau, V.J., Science 272:689-693 (1996).
Glagov, S et al., N. Engl. J. Med. 316:1371-1375 (1987).
Glukhova, M.A. et al., Am. J. Physiol. 261:78-80 (1991).
Gumbiner, B.M., Cell 84:345-357 (1996).
Hanahan, D. Science 277:48-50 (1997).
Houdebine, Louis Marie, J. Biotechnology 34:269-287 (1994).
Hynes, R.O., Cell 69:11-25 (1992).
Hynes, R.O., Curr. Opin. Genet. Dev. 4:569-574 (1994).
Ito, S. et al., "Inhibitory Effect of Type 1 Collagen Gel Containing α-elastin on Proliferation and Migration of Vascular Smooth Muscle And Endothelial Cells" Cardiovascular Surgery 5:2:176-183 (1997).
Katoh, Y. and Periasamy, M., Trends Cardiovasc. Med. 6:100-106 (1996).
Keating, M., Trends in Cardiovascular Medicine 4:165-169 (1994).
Keating, M.T., Circulation 92:142-147 (1995).
Keating, M.T., "On the Trail of Genetic Culprits in Williams Syndrome" Cardiovasc. Res. 36:134-137 (1997).
Koyama, H. et al., Cell 87:1069-1078 (1996).
Langille, B.C. and Ojhu M., Trends Cardiovasc. Med. 7:111-118 (1997).
Li, D.Y. et al., "Elastin Point Mutations Cause an Obstructive Vascular Disease, Supravalvular Aortic Stenosis" Hum. Mol. Genet. 6:1021-1028 (1997).
Li, D.Y. et al., "Elastin is an Essential Determinant of Arterial Morphogenesis" Nature 393:276-280 (1998).
Li, D.Y. et al., "Novel Arterial Pathology in Mice and Humans Hemizygous for Elastin" J. Clin. Invest. 102:10:1783-1878 (1998).
Lindahl, P. et al., Science 277:242-245 (1997).
Lohler, J. et al., Cell 38:597-607 (1984).
Machii, M. and Becker, A.E., Ann. Thorac. Surg. 64:511-515 (1997).
Mansour, S.L. et al., Nature 336:348-352 (1988).
Milnor, W.R., Principles of Hemodynamics in Cardiovascular Physiology, Oxford University Press, 184-186 (1990).
Murayama et al., AM. J. Physiol. 261(6, pt 2) H1716-H1726 (1991).
O'Connor, W.N. et al., Arch. Pathol. Lab Med. 109:179-185 (1985).
Ooyama, T. et al., "Substratum-Bound Elastin Peptide Inhibits Aortic Smooth Muscle Cell Migration in Vitro" Arteriosclerosis 7:6:593-598 (1987).
Owens, G.K., Physiol. Rev. 75:487-517 (1995).
Palmiter et al., Science 222:809-814 (1983).
Parks, William C. et al., "The Extracellular Matrix" Advances in Molecular and Cell Biology 6:133-182 (1993).
Perou, M., Arch. Pathol. 71:113-126 (1961).
Perrin, S. and Foster, J., "Developmental Regulation of Elastin Gene Expression" Crit. Rev. Eukaryot. Gene Expr. 7(1&2):1-10 (1997).
Prosser, I.W. et al., Am. J. Pathol. 135:1073-1088 (1989).
Pursel et al., Reprod. Fert. Suppl. 40, p. 235-245 (1990).
Rabinovitch, M., "Cell-Extracellular Matrix Interactions in the Ductus arteriosus and Perinatal Pulmonary Circulation" Semin. Perinatol. 20(6)531-541 (Dec. 1996).
Reitamo et al., Biological Journal, 302(pt 2):331-333 (1994).
Ross, R., Nature 362:801-809 (1993).
Saga, Y. et al., Genes Dev. 6:1821-1831 (1992).
Sato, T.N. et al., Nature 376:70-74 (1995).
Sauvage, M. et al., "Aortic Elastin and Collagen Content and Synthesis in Two Strains of Rats with Different Susceptibilities to Rupture of the Internal Elastic Lamina" J. Vasc. Res. 34:126-136 (1997).
Schwartz, S.M. et al., Physiol. Rev. 70:1177.
Schwartz, S.M. et al., Circ. Res. 77:445-465 (1995).
Seamark, R.F., Reprod. Ferts. Dev. 6:653-657 (1994).
Sechler et al., Ciba Foundations Symposium 192:148-171 (1995).
Senior, Robert M. et al., "Chemotactic Activity of Elastin-derived Peptides" J. Clin. Invest. 66:859-862 (1980).
Senior, Robert M. et al., "Val-Gly-Val-Ala-Pro-Gly, a Repeating Peptide in Elastin, Is Chemotactic for Fibroblasts and Monocytes" The Journal of Cell Biology 99:870-874 (Sep. 1984).
Shalaby, F. et al., Nature 376:62-66 (1995).
Suri, C. et al., Cell 87:1171-1180 (1996).
Tajima, Shingo, "Correlation of Elastin Expression and Vascular Smooth Muscle Cell Proliferation in vitro" Extracellular Matrix-Cell Interactions: Molecules to Diseases (Japan Scientific Societies Press) pp. 109-121 (1998).
Tassabehij, M. et al., "An Elastin Gene Mutation Producing Abnormal Tropoelastin and Abnormal Elastic Fibres in a Patient with Autosomal Dominant Cutis Laxa" Hum. Mol. Genet. 7:6:1021-1028 (1998).

Tassabehij, M. et al., "Elastin Genomic Structure and Point Mutations in Patients with Supravalvular Aortic Stenosis" *Hum. Mol. Genetics* 6:7:1029-1036 (1997).

Terpin, T. and Roach, M.R., Can. J. Physiol. Pharmacol. 65:395-400 (1987).

Thomas, K.R. and Capecchi, M.R., *Nature* 346:847-850 (1990).

Thompson, R.W., *Curr. Opin. Cardiol.* 11:504-518 (1996).

Wolinsky, H. and Glagov, S., Circ. Res. 20:99-111 (1967).

Wu, Y.-Q. et al., "Delineation of the Common Critical Region in Williams Syndrome and Clinical Correlation of Growth, Heart Defects, Ethnicity, and Parental Origin" Am. J. Med. Genet. 78:82-89 (1998).

Yamamoto, M. et al., "Increase in Elastin Gene Expression and Protein Synthesis in Arterial Smooth Muscle Cells Derived From Patients With Moyamoya Disease" Stroke 28(9):1733-1738 (Sep. 1997).

Yang, J.T. et al., *Development* 119:1093-1105 (1993).

Zheng, X. et al., *Proc. Natl. Acad. Sci. USA* 92:12426-12430 (1995).

* cited by examiner

Translocation in exon 28

Deletion of exons 28 to 36

ELASTIN-BASED COMPOSITIONS

CROSS-REFERENCE TO RELATED APPLICATIONS

This application is a continuation-in-part of U.S. application Ser. No. 09/258,217, filed Feb. 26, 1999 now U.S. Pat. No. 6,903,244, which is hereby incorporated by reference in its entirety.

This application was made with Government support under an NIH grant (Grant No. NIHK08HL03490-03) funded by the National Institutes of Health, Bethesda, Md. The U.S. Government has certain rights in this invention.

BACKGROUND OF THE INVENTION

1. Field of the Invention

The present invention relates to compositions and methods useful in the study, prevention and treatment of a variety of diseases characterized by a diminished capacity to regulate smooth muscle function. More particularly, the invention relates to compositions and methods for delivery of elastin-based compositions including elastic fibers, elastin, tropoelastin, or fragments thereof. Preferred compositions and methods of the invention are useful in the prophylaxis treatment of vascular disease.

2. Description of the Related Art

Vasculogenesis begins early in vertebrate development and culminates in the formation of a complex network of arteries, veins, and capillaries. Once formed, the gross and microscopic structure of this network is stable unless disrupted by disease. Genetic and cell culture studies have begun to identify molecular determinants of vasculogenesis, and these determinants have defined three distinct stages of vascular development (Hanahan, 1997; Folkman and D'Amore, 1996). In the first stage, splanchnic mesoderm coalesces to form simple tubes of endothelial cells. Vascular endothelial growth factor defines this stage (Shalaby et al., 1995; Fong et al., 1995; Carmeliet et al., 1996). The second stage involves the recruitment of mesenchymal cells by the endothelium, a process coordinated by angiopoietin and platelet-derived growth factor (Ferrara et al., 1996; Suri et al., 1996; Lindahl et al., 1997; Sato et al., 1995). In the third stage, mesenchyme differentiates into smooth muscle and extracellular matrix deposition begins. Transforming growth factor beta has been implicated in this stage (Folkman and D'Amore, 1996; Beck and D'Amore, 1997). After the third stage of vascular development, arterial smooth muscle cells exit the cell cycle and vascular structure is stabilized (Schwartz et al., 1990; Owens, 1995; Glukhova et al., 1991).

There is growing evidence that the extracellular matrix regulates cellular function during organogenesis. Fibronectin, vitronectin, collagen, and other extracellular matrix proteins bind to integrins on the surface of cells (Gumbiner, 1996; Hynes, 1992), providing morphogenic signals that regulate cell proliferation, migration, and differentiation (Adams and Watt, 1993; Hynes, 1994). Disruption of fibronectin in mice causes dramatic developmental abnormalities, including failure to develop a notochord and somites (George et al., 1993). Null mutations in genes encoding fibronectin receptors, or integrins, lead to embryonic or perinatal death from developmental abnormalities resembling those observed in mice lacking fibronectin (Yang et al., 1993; Yang et al., 1995). Not all cell-matrix interactions, however, are necessary for normal morphogenesis. For example, disruption of vitronectin, tenascin C, and integrin alpha 1 have no apparent effect on development (Zheng et al., 1995; Saga et al., 1992; Gardner et al., 1996).

Elastin is the dominant arterial extracellular matrix protein (Parks et al., 1993). This protein is encoded by a single gene and organized into polymers that form concentric rings of elastic lamellae around the arterial lumen. Each elastic lamella alternates with a ring of smooth muscle, forming a lamellar unit. The function of elastic fibers was thought to be structural, providing tensile strength and resiliency to the aorta and other arteries. Because of its structural role, investigators believed that disruption of elastin would lead to dissection of arteries. This view was supported by studies associating decreased elastin content and increased elastase activity with arterial aneurysms in humans and other species (Thompson, 1996; Terpin and Roach, 1987). In addition, disruption of collagen I and fibrillin, prominent arterial extracellular matrix proteins, resulted in rupture of blood vessels in mice and humans (Lohler et al., 1984; Dietz and Pyeritz, 1995). Human molecular genetic studies demonstrated, however, that ELN mutations do not cause arterial dilatation, but instead cause an obstructive arterial disease, supravalvular aortic stenosis (SVAS) (Curran et al., 1993; Ewart et al., 1993).

Obstructive vascular diseases cause over 40% of mortality in the United States. Vascular obstructive pathology consists of an accumulation of vascular smooth muscle cells and matrix components in the subendothelial space that occludes arterial lumens and restricts blood flow. Monocytes and macrophages are activated and release growth factors and cytokines at the site of injury. These peptides induce vascular smooth muscle cells to dedifferentiate and lose their contractile phenotype, migrate, proliferate, and occlude blood vessels.

Conventional therapies focus mainly on reducing the risk factors associated with obstructive vascular disease. Anti-thrombotic, anti-hypertensive, and cholesterol-lowering medications are aimed at decreasing the risk of occlusion, while beta blockers and angiotensin converting enzyme inhibitors act by reducing the workload of the heart.

The treatment of vascular stenosis remains surgical, consisting of bypass grafting and angioplasty. Over 600,000 bypass grafts are performed annually at an average cost of $45,000 per procedure. This procedure uses native vessels from the legs (saphenous veins) and breastbone (internal mammary arteries) to bypass the occluded vessels of the heart. Because bypass grafting entails open heart surgery, angioplasties have become the first line of treatment for obstructive vascular diseases. In the United States alone, this procedure is performed more than 660,000 times per year at an average cost of $20,000 per procedure. Briefly, this technique involves visualizing the obstructing lesion through angiography and relieving the obstruction by placing an intravascular balloon across the lesion and expanding it.

Unfortunately, only 60–70% of angioplasties lead to long-term (6 months) relief of arterial obstruction. In a process termed restenosis, the vascular smooth muscle cells differentiate, proliferate, and reocclude the artery following instrumentation. Many strategies have been employed to reduce and prevent vascular restenosis. However, a variety of methods of relieving the initial vascular obstruction including balloon angioplasty, atherectomy, and rotablation have not reduced the incidence of vascular restenosis. The use of metal intravascular stents in conjunction with either radioactivity or synthetic polymers has been similarly ineffective. Finally, attempts to inhibit vascular smooth muscle cell proliferation and migration using growth factors and cytokines have also not proved successful. Thus, there remains a significant need for compositions and methods useful in the prophylaxis and treatment of obstructive vascular disease.

SUMMARY OF THE INVENTION

The present invention includes a pharmaceutical composition that provides an elastin-based composition to a target site in vivo. The elastin-based composition of the invention has one or more of the following in vivo biological activities: (1) inhibition of smooth muscle cell proliferation; (2) stimulation of smooth muscle cell differentiation; and (3) regulation of smooth muscle cell migration. Elastin-based compositions having such activity include elastic fibers, elastins, tropoelastins, or fragments thereof. Elastin-based compositions can be employed in the invention in soluble or insoluble (e.g., crosslinked, precipitated, or coacervated) form. Soluble elastin-based compositions preferably have an IC50/EC50 for any of the above biological activities that they possess of less than or approximately equal to $10^{-3}$ molar (M).

Pharmaceutical compositions according to the invention can contain an elastin-based composition or one or more components that produce an elastin-based composition in vivo, such as an expression vector encoding tropoelastin or a fragment thereof. In preferred embodiments, the elastin-based composition includes a soluble elastin polypeptide, such as a recombinant tropoelastin and/or a synthetic elastin peptide. In a variation of the latter embodiment, the synthetic elastin peptide includes at least two repeats of the hexameric sequence Val-Gly-Val-Ala-Pro-Gly (SEQ ID NO: 1). (Amino acids are indicated herein using standard 3-letter or single-letter code.

In a preferred embodiment, the elastin-based composition includes an elastin matrix produced from a blood vessel. The invention also provides a novel method of producing an elastin matrix having superior purity and biocompatibility from a blood vessel.

Another aspect of the invention is a method for prophylaxis or treatment of a disorder characterized by diminished capacity to regulate smooth muscle cell function. In one embodiment, this method entails delivering an elastin-based composition to an in vivo target site. Examples of vascular diseases that can be prevented or treated by this method include atherosclerosis, restenosis, vascular bypass graft stenosis, transplant arteriopathy, aneurysm, and dissection. In preferred variations of this embodiment, the elastin-based composition is delivered to and maintained at the target site. In a second embodiment, the method entails administering an elastase inhibiter to an individual known or suspected to have a disorder characterized by diminished capacity to regulate smooth muscle cell function.

The invention additionally provides a method to screen for a drug candidate useful in the prophylaxis or treatment of such a disorder, including, for example, atherosclerosis, SVAS, or hypertension. The method involves administering a drug to an ELN +/− or ELN −/− organism or cell and determining whether the drug: (1) increases elastin mRNA or protein levels or elastin activity; (2) inhibits smooth muscle cell proliferation, stimulates smooth muscle cell differentiation, or regulates vascular smooth muscle cell migration; or (3) inhibits occlusion of arteries in said organism; and/or (4) lengthens the lifespan of said ELN −/− organism.

In one embodiment, synthesis of elastin RNA is measured in the presence of the drug as an indication of the drug's capacity to increase elastin mRNA levels. In a second embodiment, synthesis of the elastin protein is measured in the presence of the drug as an indication of the drug's capacity to increase elastin protein levels. In a third embodiment, activity of elastase is measured in the presence of the drug as an indication of capacity to increase elastin protein levels.

When screening for drug candidates suitable for preventing or treating disorders such as atherosclerosis, transplant arteriopathy, or restenosis, an ELN −/− organism or ELN −/− cell can be treated with the drug, followed by measurement of inhibition of vascular smooth muscle cell proliferation, stimulation of vascular smooth muscle cell differentiation, and/or regulation of vascular smooth muscle cell migration.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 6A and 6B show sections of mice at P0.5 immunostained with antisera against smooth muscle a-actin. The subendothelial cells in ELN −/− mice stained positively (arrow), indicating that they were smooth muscle. FIGS. 6C and 6D show sagittal sections of the ascending aorta at P2.5, stained with hematoxylin and eosin. The subendothelial cells in ELN −/− mice were longitudinally oriented (arrow), whereas normal orientation is circumferential. FIGS. 6E and 6F show aortic sections of E17.5 mice immunostained with antisera against PCNA (dark brown nuclei). The percentage of cells stained with PCNA was greater in ELN −/− mice than in ELN +/+ mice (88% vs. 35%), indicating increased cell proliferation in ELN −/− aortas. FIGS. 6G and 6H show sections of mice at P0.5 immunostained with antisera against von Willebrand factor (red). There was no evidence of endothelial damage. FIGS. 6I and 6J are sections of mice at P0.5 incubated with Masson trichrome, which stains collagen green. There was no collagen deposition.

FIGS. 7D and 7F show obliteration of the ELN −/− aortas occurs after 24 hours of incubation. FIG. 7G shows a comparison of in vivo and in vitro proliferative indices. The proliferative indices of ELN +/+ and ELN −/− aortas in organ culture (E16.5, 24 hours incubation; n=8) were comparable to those obtained in vivo (E15.5–E17.5; n=5).

FIG. 8 shows phase contrast and immunofluorescence of ELN +/+ (a–d) and ELN −/− (e–h) vascular smooth muscle cell without (a, b, e, f) and with (c, d, g, h) treatment with recombinant human tropoelastin. Contractile organization of ELN −/− vascular smooth muscle cells is absent and induced by treatment with tropoelastin.

DETAILED DESCRIPTION OF THE INVENTION

Figure 1:
FIG. 1 is a schematic illustrating the large DNA rearrangements in the human elastin gene associated with supravalvular aortic stenosis. These mutations include partial deletion of the elastin gene and chromosomal rearrangement disrupting the elastin gene. Black and white boxes indicate, respectively, exons and introns of the human elastin gene.
Figure 1:
Figure 2:
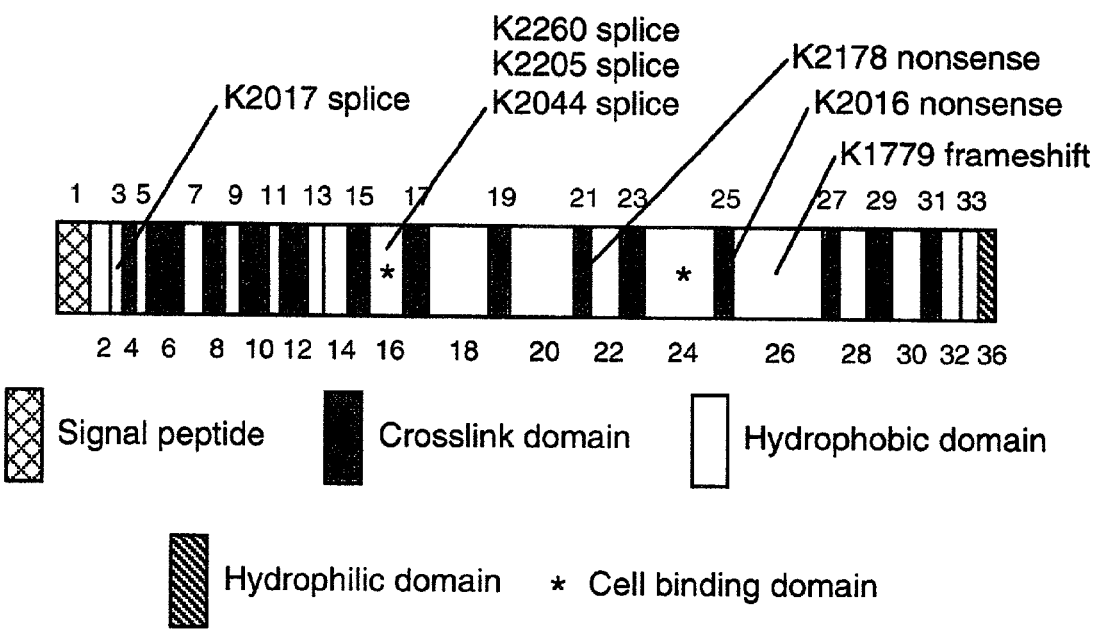
FIG. 2 is a schematic illustrating point mutations in the elastin gene product that are responsible for supravalvular aortic stenosis.

The present invention is base on a novel strategy for preventing or treating a variety of disorders characterized by inappropriate smooth muscle cell function using biocompatible forms of the extracellular matrix protein elastin that are potent regulators this function. The invention is particularly useful in the prophylaxis or treatment of vascular disease, including occlusive vascular diseases, such as vascular restenosis, atherosclerosis, and transplant arteriopathy. The significance of elastin's regulatory activity and the possibility of exploiting this activity for medical applications was previously unappreciated.

The invention provides a variety of screening methods based on the discovery that elastin-based compositions can be used to treat disorders of smooth muscle cell function. Preferred methods rely on organisms lacking function in one or both elastin genes or on cells derived from such organisms.

The present invention additionally provides pharmaceutical compositions containing biologically active elastin-based compositions. In addition to potent smooth muscle cell regulatory activity, these compositions are characterized by superior biocompatibility, making them the first elastin-based compositions suitable for medical use. Furthermore, the pharmaceutical compositions of the invention offer great flexibility with respect to form and route of administration. In addition to injection, the compositions can be used to form implants by, e.g., cross-linking the compositions in molds, dispersing the compositions in polymers, and attaching the compositions to supports.

Elastin-based compositions according to the invention can also be produced directly from blood vessels. The resulting tubular composition can be used an applications requiring a tubular or pouch-shaped implant. Tubular implants can, for example, be delivered to, and preferably maintained at, a vascular site suspected or known to be at risk for restenosis. Such implants have, for the first time, been demonstrated to prevent restenosis following angioplasty.

ELN +/− and ELN −/− Organisms

In one embodiment, the invention employs organisms that are either heterozygous (ELN +/−) or homozygous (ELN −/−) for an ELN null mutation. Such organisms are exemplified herein by ELN +/− and ELN −/− mice, but those of skill in the art appreciate that the methods of the invention can be employed with any vertebrate having such loss-of-function mutations; preferably, the methods of the invention employ a mammal. ELN +/− mice were generated by homologous recombination and were mated to produce ELN −/− mice, as described in detail in Example 1. However, similar mutations occur naturally or can be induced by other means, and the invention encompasses the use of ELN +/− and/or ELN −/− organisms, regardless of how the ELN mutations originated.

ELN −/− Organisms

ELN −/− organisms do not produce elastin. The effect of this mutation is illustrated herein in studies of ELN −/− mice, which develop aortas that become filled with an accumulation of subendothelial cells. The absence of elastin results in the uncontrolled growth of subendothelial cells in aortas and these cells eventually block the aortas. In general the blockage of arteries by atherosclerosis or restenosis, e.g., following surgery to clear a blockage, are a main cause of morbidity and mortality in industrialized nations (American Heart Association, 1996). Model systems allowing for the study of these events are extremely useful.

ELN −/− mice are an excellent model for studying vascular disease. (The terms "disease" and "disorder" are used interchangeably herein to refer to any alteration of normal anatomy or physiology.) The absence of elastin results in an absence of feedback by elastin and thus loss of regulatory control of subendothelial cells. Because of the extracellular location of elastin, the feedback must be via receptors on the subendothelial cells which interact with elastin. Regulation of subendothelial cell growth can be obtained by drugs which interact with these elastin interacting receptors. Mice which produce no elastin are a perfect model system to screen for drugs which can bind to these elastin interacting receptors and thereby regulate the proliferation, differentiation, or migration of the subendothelial cells. (As used herein, the term "drug" is defined broadly to included any agent that interacts with the human or animal body.) These mice which produce no elastin will give much cleaner results as compared to identical experiments performed with mice which do produce elastin because in the latter mice the elastin will compete with the drug thereby making the results harder to interpret because the overall effect induced by a drug will be less.

Drugs can be screened by treating newborn ELN −/− mice with the test drugs and examining various criteria such as length of life, occlusion of arteries, etc. For certain drugs it will be possible to treat the pregnant mother with test drugs before the null mutant mice are born, thereby getting the drug to the mice even earlier. Such drugs would have to be capable of reaching the developing embryos in utero. In the absence of drug these mice live only a few days and the aortas become rapidly occluded. Drugs which interact with the elastin receptors on the subendothelial cells thereby inhibiting the uncontrolled growth, stimulating the differentiation, and/or regulating the migration of the subendothelial cells will result in decreased occlusion of the aortas and increased longevity. As used with respect to the effect of compositions on cell migration, the term "regulate" refers to the capacity to stimulate cell migration toward the composition and/or to maintain cells in the vicinity of the composition. Drugs discovered by these assays are candidates for use in preventing or treating, e.g., atherosclerosis, transplant arteriopathy, or restenosis in humans. Furthermore, the drugs found to work with mice are candidates as model compounds from which similar compounds can be designed for testing in humans. (General drug screening and development methods are discussed in greater detail below.) Finally, such compounds can be used to isolate and characterize the elastin receptor itself, e.g., by binding the compound on a column to prepare an affinity column through which a cell extract can be passed. This and related methods are well known to those of skill in the art.

ELN +/− Organisms

Organisms hemizygous for the elastin gene (ELN +/−) show different effects than those which are null for the elastin gene (ELN −/−). Mice which are null for elastin have abnormal regulation of subendothelial cells which quickly grow and occlude arteries because of the absence of elastin, thereby eliminating the interaction of elastin on receptors which lead to normal, regulated growth of the subendothelial cells. By contrast, mice which are hemizygous for the elastin gene do produce elastin and therefore better regulation of subendothelial cells does occur. Nevertheless, hemizygous mice do produce aortas which are different from aortas produced by wild-type mice. The aortas are composed of layers of lamellae wherein each layer is thinner than in wild-type mice but this is at least partially compensated by the fact that the hemizygous mice produce more layers of lamellae. In these hemizygous mice, wall stress (as opposed to lack of elastin interacting with its receptor as in elastin null mice) induces growth of cells thereby causing occlusion of arteries. Such mice therefore are an excellent model for the study of SVAS and of high blood pressure. Mice hemizygous for the elastin gene can be treated with test drugs and over time the amount of occlusion or stenosis can be observed. Drugs which inhibit or result in less occlusion are useful candidates for testing in humans or as model drugs as a starting point to design drugs for preventing or treating, e.g., vascular disease associated with SVAS, atherosclerosis, or hypertension. Such drugs can act by interaction with an elastin receptor thereby regulating growth of subendothelial cells or the mechanism of action can be completely different such as activating the expression of the one good elastin gene thereby resulting in enhanced production of elastin RNA and in turn enhanced production of elastin.

Inhibition of Elastase

Too much or too active elastase can result in a shortage of elastin and lead to symptoms as seen in ELN +/− or even in ELN −/− organisms. Drugs which inhibit elastase will reverse this effect. Such drugs will be useful for treating heart disease or vascular disease resulting from the presence of too much elastase. Furthermore, even if elastase is wild-type, inhibiting elastase in individuals (e.g., mice or humans) which are ELN +/− will lead to the presence of higher elastin levels which in turn will lead to a phenotype closer to that seen in individuals which are wild-type for the elastin gene. Assays can be performed by mixing drugs with purified elastase and elastin to determine whether the drug inhibits elastase activity. Such assays are widely known by those of skill in the art. Many elastase inhibitors are known and have been published.

Drug Screening and Development

Drugs that either increase the amount of elastin by increasing production or decreasing degradation at the mRNA or protein level or that mimic elastin's regulation of smooth muscle cells are candidates for treating individuals with disorders characterized by loss of appropriate regulation of smooth muscle cells. Such drugs can be of any type, including but not limited to, nucleic acids, polypeptides or other organic molecules. Screening for such drugs can be carried out by examining the effects of drugs on elastin transcription or translation; elastin mRNA or protein degradation; proliferation, differentiation, or migration of smooth muscle cells; development and maintenance of tissues (e.g., the aorta); and survival (e.g., of ELN −/− organisms).

Screening for such drugs can be performed either in vitro (i.e., in cells or cell-free systems) or in vivo (e.g., in ELN +/− or ELN −/− organisms). The screening methods described herein discuss screening aimed at identifying drugs for the prophylaxis or treatment of humans, but these methods are applicable to screens for drugs suitable for administration to any vertebrate. For ease of discussion, the screening methods of the invention are described with respect to ELN +/− and ELN −/− mice or cells therefrom; however, these methods can employ any organism or cells having these mutations.

To promote elastin production in ELN +/− mice, drugs which promote either transcription, translation or processing of the elastin gene or protein or inhibit their degradation are desired. Assays to study transcription can be performed in vitro using ELN +/− cells or a purified elastin gene in a vector and including the regulatory regions of the elastin gene. Such a system can also be used to prepare RNA to be used in a cell-free translation system to study the effects of drugs on the translation of elastin RNA. Any drugs which promote (i.e., increase) the expression of elastin RNA or the translation of elastin or even the posttranslational processing of elastin are drug candidates for treating individuals who are hemizygous or null for functional elastin genes and/or who exhibit diminished capacity to regulate smooth muscle cell function. Such studies can be performed with any gene, but mouse or human genes are preferred. These studies can be performed by transfecting eukaryotic cells with the elastin gene or they can be performed by taking mouse or human cells and studying the effect on transcription, translation and posttranslational processing of the elastin gene and elastin gene product in the presence and absence of test drugs. Furthermore, such assays can be performed in whole animals. Elastin RNA expression can be measured in any of the above systems (i.e., cell-free, transfected cell, mouse or human cell, or whole animal) by hybridization with nucleic acid probes which bind specifically to elastin RNA under the specified hybridization conditions using any convenient hybridization assay, such as a Northern blot. A variety other suitable methods for measuring RNA expression are known to those of skill in the art. The elastin gene product can be quantified using antibodies specific for elastin.

Drug screening need not be performed by evaluating changes at the molecular level, rather screening can be performed by anatomical evaluation or by measuring length of life, especially for mice which are ELN −/−. Mice can be treated with drugs either beginning at birth or preferably, as discussed above, before birth. Not all drugs will be accessible to developing embryos in utero, but those drugs which do cross the placenta can be tested by administering drug to the pregnant mother. In the absence of drug, all mice which are ELN −/− die within four days of birth. Screening drugs with such mice can be as simple as crossing hemizygotes to produce the null mice, treating with drug either at or prior to birth, and determining whether any of the mice which survive longer than 4 days are ELN −/−. When such mice are found, the administered drug is a drug candidate for further testing or as a model from which to design related drugs.

Rather than observing life span, mice can be treated with test drugs and the degree of occlusion in the aortas can be examined. For ELN +/− mice this will be enhanced by either causing the mice to become hypertensive or using a strain of mouse which is hypertensive. Drugs which result in mice with less occlusion of their aortas as compared to control mice which were not given drugs are candidate drugs for further testing or as models from which to design related drugs. An alternative assay is to examine the thickness of each lamellar layer in the aortas. Drugs which increase the thickness of each layer as compared to control hemizygous mice not administered drugs are drugs which are candidates for further testing or as models from which to design related drugs.

In whole-animal studies, test drugs are typically administered by the same route to be used in the prophylaxis or treatment of the disorder for which the drug is sought. Thus, for example, drugs for treating or prevention vascular restenosis, atherosclerosis, or transplant arteriopathy are conveniently tested by intravascular delivery. In an exemplary embodiment, a support (such as a stent) coated with the test drug is inserted at a vascular site known or suspected to be at risk for disease. Additional routes of administration for test drugs include those described below for pharmaceutical compositions of the invention.

Following identification of a substance which modulates or affects an activity as described above, the substance may be further developed to enhance desired activities and/or specificity, minimize side or toxic effects, facilitate delivery, etc.

The screening methods of the invention are particularly useful for identifying drug candidates that mimic elastin's activity. Such an elastin mimetic can be a peptide or a non-peptide. Non-peptide small molecules are often preferred for many in vivo pharmaceutical uses. Accordingly, a mimetic or mimic of the elastin may be designed for use in a pharmaceutical composition similar to those described below.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g. by substituting each residue in turn. Alanine scans of peptide are commonly used to refine such peptide motifs. These parts or residues constituting the active region of the compound are known as its "pharmacophore"

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variation of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

A drug identified using a screening method of the invention can be formulated in a pharmaceutical composition as described below for administration to prevent or treat a disorder characterized by diminished capacity to regulate smooth muscle cell function. To treat vascular disease, for example, such drugs can be attached to supports, such as stents, which can be inserted in a blood vessel such as an artery. Such stents inhibit vascular smooth muscle cell proliferation and/or stimulate differentiation and/or regulate migration and are thus particularly useful to treat or prevent atherosclerosis, restenosis, vascular bypass graft stenosis, transplant arteriopathy, aneurysm, and dissection. The methods of the present invention thus extend to preparing a pharmaceutical composition including a drug identified in a screening method of the invention and administering such a composition to an individual.

Compositions and Methods for Prophylaxis or Treatment of Conditions Characterized by Disorders of Smooth Muscle Cell Function The invention provides a pharmaceutical composition useful in the prophylaxis or treatment of conditions characterized by disorders of smooth muscle cell function, such as obstructive vascular disease. As used herein, the term "pharmaceutical composition" refers to a composition that is biocompatible. Biocompatible compositions or materials are sufficiently free of immunogenic, inflammatory, or otherwise toxic components to be tolerated by a recipient long-term (e.g., at least about 3 weeks) as well as acutely. Preferred pharmaceutical compositions are tolerated by the recipient for at least about 6 weeks, more preferably at least about 3 months, and most preferably at least about 6 months.

A pharmaceutical composition of the invention provides an elastin-based composition to a target site in vivo. The pharmaceutical composition can either contain the elastin-based composition or produce such a composition in vivo, for example by expressing, or otherwise generating, the composition at the target site.

The invention also includes methods of making such pharmaceutical compositions, as well as methods of using these compositions to prevent or treat disorders characterized by a diminished capacity to regulate smooth muscle cell function.

Elastin-Based Compositions

The elastin-based composition of the invention is a potent regulator of the proliferation, differentiation, and/or migration of smooth muscle cells in vivo. More specifically, this composition is capable of inhibiting proliferation, stimulating differentiation, and/or regulating migration. Typical elastin-based compositions share all three biological activities, but the invention encompasses compositions having only one or two of these activities.

The effects of elastin-based compositions on proliferation can be tested using any elastin-responsive cells, such as, for example, fetal calf ligament fibroblasts, murine vascular smooth muscle cells, cells from the human melanoma cell line A2058, and human monocytes. The cells can be cultured with the composition, and the increase in cell number over one to fourteen days can be compared to that observed with untreated control cells. Migration and differentiation are conveniently tested using vascular smooth muscle cells obtained from ELN –/– mice. Exemplary assays of migration and differentiation are described in Examples 4 and 5, respectively.

The elastin-based composition can include one or more elastic fibers, elastins, tropoelastins, or a fragment thereof. Elastin is the predominant protein of mature elastic fibers. Tropoelastin is a single-chain polypeptide precursor that is crosslinked to form elastin. Tropoelastin contains alternating hydrophobic domains and crosslinking domains characterized by stretches of alanines interrupted by lysines. The polypeptide chains in such compositions and fragments of these polypeptide chains are collectively referred to herein as "elastin polypeptides." Elastin polypeptides can be used in the invention in soluble form or can be crosslinked, precipitated, or coascerated.

Elastin-based compositions useful in the invention include elastin polypeptides having native amino acid sequences (i.e., the sequence present in natural tropoelastins) as well as amino acid sequence variants. (As used herein, the term "polypeptide" includes short peptides.) However, preferred elastin-based compositions typically include elastin polypeptides having amino acid sequences that share at least 80%, preferably at least 90%, and more preferably at least 95% sequence identity with a native tropoelastin. Sequence identity is determined, for this purpose, as follows. The amino acid sequences are aligned (introducing gaps as necessary) to maximize sequence identity over the co-aligned regions of the polypeptides. The number of residues in a variant amino acid sequence that are the same as the corresponding (i.e., aligned) residues in the native tropoelastin sequence is divided by the total number of amino acids in the variant amino acid sequence over the co-aligned region.

Preferably, amino acid sequence differences between a variant amino acid sequence of the invention and the native tropoelastin that shares the greatest sequence identity with the variant represent conservative amino acid substitutions. The term "conservative amino acid substitution" is used herein to refer to the replacement of an amino acid with a functionally equivalent amino acid. Functionally equivalent amino acids are generally similar in size and/or character (e.g., charge or hydrophobicity) to the amino acids they replace. Amino acids of similar character can be grouped as follows:

(1) hydrophobic: His, Trp, Tyr, Phe, Met, Leu, Ile, Val, Ala;
(2) neutral hydrophobic: Cys, Ser, Thr;
(3) polar: Ser, Thr, Asn, Gln;
(4) acidic/negatively charged: Asp, Glu;
(5) charged: Asp, Glu, Arg, Lys, His;
(6) basic/positively charged: Arg, Lys, His;
(7) basic: Asn, Gln, His, Lys, Arg;
(8) residues that influence chain orientation: Gly, Pro; and
(9) aromatic: Trp, Tyr, Phe, His.

The following table shows exemplary and preferred conservative amino acid substitutions.

| Original Residue | Exemplary Conservative Substitution | Preferred Conservative Substitution |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Asn |
| Ile | Leu, Val, Met, Ala, Phe | Leu |
| Leu | Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala | Leu |

The species type of the elastin-based composition (or the type to which the composition is most closely related) depends on the application. Elastin-based compositions can be derived from (or related to those derived from) any vertebrate. However, for most applications, these proteins are derived from (or related to) mammalian sources, such as, for example, porcine, bovine, equine, or primate sources. For administration to humans, human elastin polypeptides (or variants thereof) are preferred.

"Fragments" of elastin fibers, elastins, or tropoelastins include any polypeptide having a sequence of at least about 5, and preferably at least 6 amino acids identical to a native tropoelastin sequence. The statements above about sequence identity and conservative amino acid substitutions above apply to fragments longer than 6 amino acids. Fragments useful in the invention are typically less than about 100 amino acids, and preferably less than about 50 amino acids. Preferred fragments include an amino acid sequence that is repeated in a native tropoelastin sequence, such as the hexameric sequence Val-Gly-Val-Ala-Pro-Gly (SEQ ID NO: 1). Generally, more than one such repeat sequence is included in the fragments of the invention, and preferred fragments include more than about 5 repeat sequences. In an exemplary, preferred embodiment, a synthetic elastin peptide contains 6 repeats of the hexameric sequence Val-Gly-Val-Ala-Pro-Gly (SEQ ID NO: 1). Such repeat sequences may be joined end to end or may be separated by intervening sequences, as in native tropoelastins. An exemplary, preferred peptide containing 6 repeats of the hexameric sequence and a linker hexapeptide (i.e., 42 amino acids in total) is described in Example 2.

As used herein, the terms "elastin fiber," "elastin," "tropoelastin" and "fragments" of these materials include derivatives of the native forms of these proteins (or of their amino acid sequence variants, as discussed above) that retain one or more of the three biological activities discussed above (i.e., inhibition of proliferation, stimulation of differentiation, or regulation of migration of smooth muscle cells). The invention therefore encompasses materials that have been derivatized, for example, to increase their suitability for a particular application of the invention. The term "derivatized" is used herein to denote the modification of one or more chemical groups, which includes, e.g., linkage to other polypeptides by production of fusion proteins, in addition to modifications produced by reaction of a chemical group with another moiety.

For example, in particular embodiments, the elastin-based compositions are linked to targeting moieties, such as antibodies or cell specific ligands, to direct the compositions to specific target sites. In alternative embodiments, targeting is carried out by activating an inactive precursor at the target site. Thus, elastin-based compositions also include forms of elastin fibers, elastin, tropoelastin, or fragments thereof that are derivatized to form inactive precursors. The precursor is converted to an active form by an activating agent produced in, or targeted to, the cells to be treated. See, for example, EP 425,731A and WO 90/07936.

Elastin-based compositions designed for sustained-release can be produced by attaching a polyalkylene glycol (e.g., polyethylene glycol [PEG]) to elastin polypeptides, typically via e-amino groups. Attachment of PEG to proteins is a well-known means of reducing immunogenicity and extending in vivo half-life (see, e.g., Abuchowski, J., et al. (1977) J. Biol. Chem. 252:3582–86). Any conventional "pegylation" method can be employed, provided the "pegylated" elastin-based composition retains the ability to regulate smooth muscle cell function as described above.

As described in greater detail below, tropoelastin polypeptides be "derivatized" by crosslinking to form matrices having a size and shape suited to a specific application.

In other embodiments, in which elastin-based compositions are attached to supports, elastin polypeptides in the compositions may be derivatized to facilitate attachment to the support. Any conventional method for derivatizing polypeptides that does not destroy the desired biological activity of such compositions can be used for this purpose.

Preferred soluble elastin-based compositions of the invention inhibit smooth muscle cell proliferation and/or stimulate smooth muscle cell differentiation and/or regulate smooth muscle cell migration with an IC50/EC50 that is less than or approximately equal to $10^{-3}$ M. (The IC50 is the concentration that produces half of the maximal inhibition, and the EC50 is the concentration that produces half of the maximal stimulatory effect.) Generally, IC50/EC50s for soluble elastin-based compositions according to the invention are greater than about $10^{-15}$ M and can be, e.g., $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, or $10^{-14}$ M.

Elastin-based compositions according to the invention are generally at least about 85% pure elastin, and preferably at least about 90%, more preferably at least about 95%, and most preferably about 98–99% pure. Purity can be assessed by any standard method. For example, the purity of tropoelastin, and elastin can be assessed by running a reverse-phase HPLC amino acid analysis, according to a modification of the method described by Heinrikson and Meredity (Anal. Biochem. (1984) 137:380–8). Briefly, the elastin preparations are hydrolysed for 16 hours at 110° C. using 6 N HCl, the acid volatilized and the dried amino acids derivatized with phenylisothiocyanate. The derivatized amino acids are then analyzed by reverse-phase HPLC using an acetate/acetonitrile gradient, a K18 Pico Tag® column (Waters) at 40° C. and an HPLC-system (Kontron) with UV-detection at 254 nm. The measurement of desmosine and isodesmosine level, characteristic cross-linking amino-acids of elastin purified from tissues, is used as a measure of elastin content. Impurities such as collagen fibrils, can be assessed and quantified by measuring the levels of the cross-linked amino acids, pyridinoline and deoxypyridinoline.

Elastin fibers and elastin can be obtained from natural sources using conventional techniques. Elastin can also be produced by enzymatic crosslinking of tropoelastin. Tropoelastin is generally produced using standard recombinant techniques. An exemplary, preferred method for expressing and purifying recombinant tropoelastin is described in Example 3. Elastin fragments can be generated by standard techniques, including chemical or enzymatic (e.g., elastase) digestion of elastin or by crosslinking of tropoelastin fragments. The latter can be produced by chemical or enzymatic digestion of tropoelastin or as synthetic peptides. Amino acid sequence variants of elastin polypeptides are generally produced recombinantly or synthetically.

Derivatives of elastin fibers, elastins, tropoelastins, or fragments are produced using standard methods (e.g., chemical, enzymatic, thermal, or radiation-based techniques). Glutaraldehyde is conveniently employed for chemical crosslinking, but other suitable crosslinking agents (e.g., biocompatible epoxy compounds) are well known. Radiation-induced crosslinking is preferably carried out by exposing compositions of the invention to gamma-irradiation from a Cobalt-60 source. Crosslinking with radiation can be facilitated by adding a radiation crosslinking agent, such as a thiourea or the like to the reaction. The amount of irradiation can range, for example, from 10 to 100 MRAD, with 25 MRAD being preferred. The amount of gamma-irradiation selected for a given application will vary depending on the desired strength of the crosslinked composition (see Aprahamian, J. Biomed. Mat. Res. 21:965 (1987)).

In one embodiment, the elastin-based composition is an elastin matrix produced from a blood vessel. A typical mammalian blood vessel consists of an intimal layer, surrounded by a medial layer, which is itself surrounded by an advential layer. The intima includes a layer of endothelial cells lining the lumen of the blood vessel, a subendothelial matrix layer consisting of basement membrane and other extracellular matrix components, and an internal elastic lamellar layer. The media is composed of alternating layers of vascular smooth muscle cells and elastic lamellae. Most of the elastin in the vessel is found in the subendothelial matrix layer, specifically, in the internal elastic lamina and in the medial layer.

An elastin matrix according to the invention is substantially free of cells, and other non-elastin components, such as collagen, for example. The elastin matrix differs from conventional prostheses produced from blood vessels in that substantially all components other than elastin have been removed.

The elastin matrix is prepared by obtaining a blood vessel, generally an arterial segment, from a vertebrate species, preferably a mammalian species including, but not limited to, porcine, bovine, equine, or primate species, including humans. Preferably, the blood vessel is derived from the same species as the intended recipient of the elastin matrix.

The blood vessel is obtained by harvesting an artery of the desired size and thickness using aseptic surgical technique. Blood vessels can be processed as tubular segments that yield a tubular elastin matrix. Alternatively, blood vessels can be opened and shaped to yield sheets suitable, e.g., for mounting on a support of any shape. Preferably, however, when producing a tubular elastin matrix, the blood vessel is selected so as to yield a tubular matrix having the desired diameter so that subsequent manipulations (other than adjustment of length) can be avoided.

Blood vessels suitable for producing an elastin matrix include carotid, internal mammary, subclavian, axillary, brachial, radial, ulnar, renal, iliac, popliteal, tibial, and femoral arteries, as well as descending aorta and saphenous veins. Carotid arterial segments, for example, can be isolated through a single midline cervical incision. The source tissue can be frozen, but should be thawed before isolation of the blood vessel.

After dissection from the source tissue, the blood vessel is generally rinsed in a physiological saline solution at about 4° C. In addition to normal saline (0.9% NaCl), any of a number of physiological balanced salt solutions can be employed, including, for example, Dulbecco's phosphate-buffered saline, Earle's balanced salt solution, Hanks' Balanced Salt Solution (HBSS), or phosphate buffered saline (PBS). Preferably, the saline solution contains a standard bacteriostatic agent, such as 0.9% benzyl alcohol.

After rinsing, loose adipose tissue and adventitia are removed from the blood vessel. If a tubular matrix is desired, a method that does not disrupt the underlying the internal elastic lamina is preferably employed. For example, a superficial cut in the outer layer of the vessel can be made and the advential layers pulled off with forceps using a dissecting microscope. Alternatively, the adventitia can be pulled and cut away with dissecting scissors. Removal of the adventitia is generally carried out in a physiological buffered saline solution, preferably one containing a detergent, such as, for example, 0.1% Tween-100 in PBS.

After loose adventitia is removed, the vessel is washed briefly in a physiological saline solution to remove residual blood inside lumen. Washing is conveniently carried out by agitating the vessel for 5 minutes at room temperature.

The blood vessel is then treated with a detergent solution to lyse and extract cellular material. The detergent solution is preferably an aqueous solution containing between about 0.1 and about 10% (wt/vol) of an ionic denaturing detergent. Suitable detergents include sodium dodecyl sulfate (SDS), sodium deoxycholic acid, and alkyl ($C_9$–$C_{13}$) sodium sulfate. The detergent solution generally contains a protease inhibitor such as ethylenediaminetetraacetic acid (EDTA), marimastat, indomethacin, doxycycline, or any other matrix metalloproteinase (MMP) inhibitor. An exemplary, preferred detergent solution contains 1% SDS and 5 mM EDTA. The vessel is incubated at elevated temperature with gentle agitation until cell lysis and extraction are achieved. This step is generally carried out at between about 35° C. to about 40° C. The time required for detergent treatment depends on the temperature. At 37° C., good results are achieved with overnight (e.g., 15–18 hr.) incubation. After detergent treatment, the blood vessel is washed to remove the detergent. Washing is generally carried out by gentle agitation for 1–2 hours at room temperature. Multiple wash changes are preferred to minimize the amount of residual detergent.

Detergent treatment is followed by treatment with an alkaline solution to solubilize and remove collagenous matter. The alkaline solution is preferably an aqueous solution containing a base at a concentration of between about 0.1 and about 6 N. Suitable bases include, for example, potassium hydroxide and sodium hydroxide. The vessel is gently agitated at elevated temperature in the alkaline solution until the majority of collagen residues are digested away. With weaker bases, sonication can facilitate collagen solubilization. This incubation is generally carried out at between about 22° C. to about 80° C. The higher the temperature, the shorter the time required for this step. Accordingly, alkaline treatment is conveniently carried out for 10 min. at 60° C. in 5 N potassium hydroxide. After alkaline treatment, washing is carried out as described above.

Any remaining adventitia is removed after alkaline treatment. Typically, at this point in the method, the vessel still contains an outer adventitial layer. Using fine-tip dissecting forceps, this outer layer is separated and removed from the inner elastin layer using caution not to perforate or tear the elastin matrix. The result of this process is a tubular matrix containing elastin and trace amounts of residual collagen. A final collagen-removal step is employed to remove the remaining collagen. Any method that removes collagen and leaves the elastin matrix intact can be used. Examples include autoclaving for a short period of time (e.g., 30 min. at 225° C.) or collagenase treatment. Collagenase is commercially available from Roche, Inc., (Indianapolis, Ind.) or Sigma (St. Louis, Mo.). Immersion in 0.5 mg/mL collagenase in Hanks Balanced Salt Solution (HBSS) for 1 hr. at 37° C. is typically sufficient to remove residual collagen. The resulting elastin matrix is washed, preferably multiple times, with water (e.g., distilled, deionized water), followed by sterilization.

The elastin matrix can be sterilized by any method that inactivates any endotoxin contaminants without degrading elastin. Preferably, the matrix is washed with a 70% ethanol solution. The elastin matrix is then generally stored at 4° C. in fresh 30% ethanol solution.

Production of Elastin-Based Compositions In Vivo

As noted above, pharmaceutical compositions according to the invention can contain an elastin-based composition or produce one in vivo, preferably at the target site. In the latter embodiment, the elastin-based composition can be produced, for example, using an appropriate expression vector. The vector can be targeted to the specific site to be treated (e.g., the aortic cells), or it can contain regulatory elements that activate expression in specific target cells. In one embodiment, the pharmaceutical composition simply includes a nucleic acid molecule encoding an elastin-based composition in an expression vector, e.g., a viral vector. In an alternative embodiment, the pharmaceutical composition includes a cell-based delivery system containing the expression vector. Examples of such systems are described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635. Such cell-based delivery systems are designed to be implanted in a patient's body at the target site.

Pharmaceutical Formulations

The pharmaceutical compositions of the invention include elastin-based compositions, nucleic acids encoding them, or drugs identified using the screening methods of the invention (collectively termed "the active agents") formulated, in one embodiment, according to conventional pharmaceutical compounding techniques. See, for example, *Remington's Pharmaceutical Sciences,* 18th Ed. (1990, Mack Publishing Co., Easton, Pa.). Pharmaceutical formulations of the invention can contain the active agent or a pharmaceutically acceptable salt of the active agent. These compositions can include, in addition to an active agent, a pharmaceutically acceptable excipient, carrier, buffer, stabilizer or other material well known in the art. Such materials should be non-toxic and should not interfere with the efficacy of the active agent. The carrier may take a wide variety of forms depending on the route of administration, e.g., intravenous, oral, intrathecal, epineural or parenteral.

For oral administration, active agents can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract.

For parenteral administration, the active agent is dissolved (e.g., soluble elastin) or suspended in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like.

Preferred embodiments include sustained-release pharmaceutical compositions. An exemplary sustained-release composition has a semipermeable matrix of a solid biocompatible polymer to which the elastin-based composition is attached or in which the composition is encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(−)-3-hydroxybutyric acid. Polymer matrices can be produced in any desired form, such as a film, or microcapsules.

Other sustained-release compositions include a liposomally entrapped elastin-based composition. Liposomes suitable for this purpose can be composed of various types of lipids, phospholipids, and/or surfactants. These components are typically arranged in a bilayer formation, similar to the lipid arrangement of biological membranes. Liposomes containing elastin-based compositions are prepared by known methods, such as, for example, those described in Epstein, et al. (1985) PNAS USA 82:3688–92, and Hwang, et al., (1980) PNAS USA, 77:4030–34.

The pharmaceutical compositions of the invention also encompass combinations of an active agent, as described above, with one or more additional drugs. For treating vascular disease, for example other drugs that regulate vascular smooth muscle cell proliferation, differentiation, and/or migration can be included in the elastin-based compositions, as can anticoagulants, such as heparin; antiplatelet drugs, such as hirudin; and vasodilators.

In a preferred embodiment, elastin-based compositions are seeded with cells such as smooth muscle cells either in vitro or in vivo. In vitro, standard cell culture techniques can be used to seed the elastin-based compositions of the invention. For example, a tubular elastin matrix can be seeded with vascular smooth muscle cells to form an bioengineered vessel useful in standard vascular bypass procedures. Unseeded elastin-based compositions can also be placed and maintained at a site of vascular disease using standard angioplasty techniques. Invasion of surrounding vascular smooth muscle cells within the instrumented vessel then seeds the elastin-based composition in vivo.

Articles Formed from Elastin-Based Compositions

Pharmaceutical compositions according to the invention include implants, i.e., compositions or device that are delivered directly to a site within the body and are, preferably, maintained at that site to provide sustained regulation of smooth muscle cell function. Implants suitable for this use include elastin-based compositions in the form of shaped articles designed for implantation. That is, elastin-based compositions can be molded to a suitable size and shape for specific applications. The resulting compositions can be crosslinked as described above or can simply be precipitated or coacervated and dried.

For example, sheets of elastin-based compositions having desired thicknesses can be prepared by using appropriate molds. Such sheets can be made in thicknesses ranging, for example, from about 200 microns to about 5 mm. Sheets designed for use in arterial stents or patches can be thinner (e.g., about 100 μm to about 1000 μm).

Elastin-based compositions can also be molded into tubular segments, for example, by injecting solutions or suspensions of the compositions into tubular molds. The elastin-based composition can be crosslinked before or after removal of the mold. Tubular segments of different inner and outer diameters, as well as of different lengths, can be prepared using this approach by varying the diameters of inner and outer tubes. Tubular segments of such elastin-based compositions can be used in the treatment of vascular disease, as discussed above for elastin tubes prepared from blood vessels. The elastin-based compositions can also molded using pressure (e.g., vacuum or centrifugal force) to produce a desired shape.

Elastin-Based Compositions Attached to Supports

The pharmaceutical compositions of the invention also include implants comprising an elastin-based composition is attached to a biocompatible support that can be delivered to and, preferably, maintained at a target site, such as a vascular site suspected or known to be at risk for obstructive disease.

The support can be made from any biologically compatible material, including polymers, such as polytetrafluorethylene (PFTE), polyethylene terphthalate, (Dacron®), polypropylene, polyurethane, polydimethyl siloxame, fluorinated ethylene propylene (FEP), polyvinyl alcohol, poly(organo)phosphazene (POP), poly-1-lactic acid (PLLA), polyglycolic/polylactic acid copolymer, methacrylphosphorylcholine and laurylmethacrylate copolymer, phosphorylcholine, polycaprolactone, silicone carbide, cellulose ester, polyacrylic acid, and the like, as well as combinations of these materials. Metals, such as stainless steel, nitinol, titanium, tantalum, and the like, can also be employed as or in the support.

Preferably, the support is sufficiently porous to permit diffusion of elastin-based compositions or products thereof across or out of the support. More preferably, the support is also sufficiently permeable to allow infiltration of host cells.

The support can be coextensive with the elastin-based composition, but need not be. In one embodiment, for example, a tubular elastin-based composition (e.g., one produced from a blood vessel) is attached to one or more rings that help prevent collapse of the tube. In a preferred version of this embodiment, a tubular elastin-based composition has a ring attached to each open end of the tube so that the lumen of the tube is aligned with the space circumscribed by the ring.

Supports can provide pharmaceutical compositions of the invention with desired mechanical properties. Those skilled in the art will recognize that minimum mechanical integrity requirements exist for implants that are to be maintained at a given target site. Preferred intravascular implants, for example, should resist the hoop stress induced by blood pressure without rupture or aneurysm formation.

The size and shape of the support is dictated by the particular application. If the support is to be maintained at a vascular site, a tubular support is conveniently employed. In a preferred embodiment, the support tubular is a support designed to help maintain blood vessel patency, such as, for example, vascular stent. Preferably, the stent is on one that can be loaded onto a conventional angioplasty balloon catheter for implantation. Stents suitable for this purpose are available commercially from a variety of sources, including Medtronic/AVE (Santa Rosa, CA), Guidant (Indianapolis, Ind.), Cook Cardiology (Bloomington, Ind.), and Johnson & Johnson/Cordis (New Brunswick, N.J.).

Example 7 illustrates an embodiment in which elastin matrices were prepared from porcine carotid artery segments, which are unbranched and average 3–4 mm in internal luminal diameter and between 8–10 cm in length. The elastin matrices so produced were cut to length and attached to 3.5 mm×16 mm stents.

"Attachment" of elastin-based compositions to support is conveniently achieved by adsorption of the compositions on a support surface. However, any form of attachment, e.g., via covalent or non-covalent bonds is contemplated. In one embodiment, the elastin-based composition is prepared as a solution, preferably containing a carrier, such as bovine serum albumin (BSA). This solution is crosslinked using an agent such as glutaraldehyde, gamma irradiation, or a biocompatible epoxy solution and then applied to the surface of the support by coating or immersion.

Alternatively, elastin-based compositions can be mechanically entrapped in a microporous support (e.g., ePTFE). The elastin-based composition solution employed for this method need not be crosslinked. After wetting the support (e.g., with 100% ethanol), the solution is forced into the pores of the support using positive or negative pressure. For tubular supports, a syringe containing the solution can be attached to the tube so that the solution is forced into the lumen of the tube and out through the tube wall so as to deposit the elastin-based composition on internal and external support surfaces.

Elastin-based compositions can also be dissolved and suspended within a biocompatible polymer matrix, such as those described above, that can then be coated on a support or prosthetic device. Preferably, the polymerized matrix is porous enough to allow cellular interaction with the elastin-based composition.

In an exemplary, preferred embodiment, an elastin matrix is employed as the elastin-based composition. Aseptic technique is used during attachment of the elastin matrix to the support and implantation of the elastin matrix/support assembly. The elastin matrix is removed from storage and rehydrated in physiological saline, preferably containing an antibiotic, followed by heparinized physiological saline. Rehydration is usually complete after about 30 min. in each solution (preferably with multiple changes of solution). The elastin matrix is then sterilized, preferably by $^{137}$Cs-irradiation for 30 minutes (≈8k RAD), but any sterilization method that does not significantly damage the elastin matrix can be used.

The sterile, heparinized elastin matrix is then mounted on the support, and excess elastin matrix is cut away from borders of the support. A dissecting microscope facilitates this process. The elastin matrix/support assembly is then dried sufficiently to secure the elastin matrix to the support surface, taking care not to allow complete drying of the elastin matrix. For an elastin matrix/stent assembly such as that discussed above, the drying step can be carried out for 20 min. under vacuum (e.g., 10 mm Hg).

If the elastin matrix/support assembly is intended for intravascular use, the elastin matrix must be firmly secured to the support to ensure that intravascular flow disturbances do not occur. Furthermore, any means used to anchor the elastin matrix to the support must be biocompatible. For example, conventional suture materials should generally not be used to secure the elastin matrix to a support since such materials induce granuloma formation.

Elastin matrix/support assemblies intended for intravascular use preferably have the matrix attached to the outside surface of a tubular support. The matrix could also be attached to the interior of the support, provided the matrix was sufficiently firmly attached to the support. Loose matrix would predispose to intravascular flow disturbances and could result in thrombus formation.

In a preferred embodiment, the support is enclosed in a biocompatible sheath. The term "sheath" is used herein to refer to a second support that surrounds a first support. In a particularly preferred variation of this embodiment, an elastin-based composition is "sandwiched" in between a support and a sheath. The elastin-composition can be attached to either the support or the sheath using any of the attachment methods described above.

In an exemplary, preferred embodiment, the invention provides a pharmaceutical composition including a sheath encircling a tubular support, to which an elastin-based composition is attached. Such a composition can be prepared from any of the elastin-based compositions of the invention, but is particularly preferred when the elastin-based composition is an elastin matrix. The sheath is applied to the elastin matrix/support assembly after drying to help secure the elastin matrix. This sandwich configuration ensures that the elastin matrix will not be lost during deployment or implantation.

The considerations affecting the selection of a sheath size, shape, and material are generally the same as those discussed above with respect to supports.

Articles of Manufacture and Kits

The invention also provides articles of manufacture including pharmaceutical compositions of the invention and related kits. The invention encompasses any type of article including a pharmaceutical composition of the invention, but the article of manufacture is typically a container, preferably bearing a label identifying the composition contained therein. The container can be any formed from any material that does not react with the contained composition and can have any shape or other feature that facilitates use of the composition for the intended application. A container for a pharmaceutical composition of the invention intended for parental administration generally has a sterile access port, such as, for example, an intravenous solution bag or a vial having a stopper pierceable by a hypodermic injection needle.

Kits of the invention generally include one or more such articles of manufacture and preferably include instructions for use. Preferred kits include one or more devices that facilitate delivery of a pharmaceutical composition of the invention to a target site. For example, kits containing tubular pharmaceutical compositions intended to treat vascular disease can also include an angioplasty balloon catheter for implantation.

Prophylaxis or Treatment Methods

The invention also includes a method for prophylaxis or treatment of a disorder characterized by diminished capacity to regulate smooth muscle cell function. With respect to vascular disorders, the method can be used to treat or prevent, for example, atherosclerosis, restenosis, vascular bypass graft stenosis, transplant arteriopathy, aneurysm, and dissection.

The method entails administration of a pharmaceutical composition of the invention so as to provide an effective amount of an elastin-based composition at a target site. Preferably, the pharmaceutical composition is delivered to and maintained at the target site. As used with reference to such compositions, the term "effective amount" refers to an amount that produces any prophylactic or therapeutic effect. In the case of vascular disease, a prophylactic or therapeutic effect includes, but is not limited to, prevention or reduction of atherosclerosis, restenosis, stenosis, arteriopathy, and anastomotic intimal hyperplasia, as well as repair of vascular pseudoaneuyrsm, aneurysm, and arterial dissection. Examples 7 and 8 demonstrate that the compositions of the invention reduce the risk of arterial restenosis.

Preferably, compositions of the invention are administered so as to provide a dose equivalent to $10^{-8}$ M Val-Gly-Val-Ala-Pro-Gly (SEQ ID NO: 1) or 100 ng/ml tropoelastin (or tropoelastin fragment) at a target site, such as a vascular site suspected or known to be at risk for obstructive disease. The actual amount of pharmaceutical composition administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the specific formulation, the route of administration, the target site, and other factors well known to practitioners. Examples of standard techniques and protocols can be found in *Remington's Pharmaceutical Sciences*.

The target site can be any site known or suspected to be at risk for disease based on inappropriate regulation of smooth muscle cell function. In a preferred embodiment, an elastin-based composition is delivered directly to a target site. In the case of a vascular site suspected or known to be at risk for vascular disease, intravascular delivery is preferred, and the use of an implant, such as those described above is particularly preferred. In a variation of this embodiment, the implant is delivered to and maintained at the vascular site. In the case of obstructive vascular disease, an implant configured to help maintain blood vessel patency is most preferred. Implants can also be employed as an artificial blood vessel that is grafted in place of a damaged vessel or used for vascular bypass. For example, a tubular elastin composition, such as a tubular elastin matrix, can be employed as an artificial blood vessel for coronary artery bypass grafting or other standard vascular grafting interventions. Preferably, such implants are seeded with vascular smooth muscle cells in vitro or are designed to allow in vivo seeding.

Implantation is performed using standard techniques. For example, catheter delivery systems can be employed to implant a many of the pharmaceutical compositions of the invention. As discussed above, an intravascular stent can be pre-mounted upon a deflated balloon catheter. The balloon catheter can be maneuvered into the desired arterial or venous location, and the balloon can then be inflated, pressing the stent against the vessel wall. The balloon can then be deflated and removed leaving the stent in place. A protective sleeve (e.g., of plastic) can be used to protect the stent during its passage to the vessel and then withdrawn once the stent is in the desired location.

In an alternative, preferred embodiment, the elastin-based composition is produced at the target site, for example by activation of a precursor form or by expression of a vector containing encoding the elastin-based composition. Precursor-activator systems can be designed based on conventional "prodrug" therapies. Expression systems can be designed based on standard gene therapy techniques, including those that use viral vectors, especially retroviral vectors, such as those derived from adenoviruses.

Vectors expressing elastin-based compositions can be injected at the target site, as can cells containing such vectors. Alternatively, such vectors or cells can be introduced ex vivo into tissue grafts, which are then implanted. For example, transfer of a tropoelastin expression vector into the endothelium and vascular media of a saphenous vein graft can be achieved using an adenoviral vector according to the following exemplary procedure. The saphenous vein is removed and placed in a sterile physiological medium (e.g., 10 mM Tris-HCl, 125 mM NaCl, 1 mM $MgCl_2$, pH 7.4) containing adenovirus bearing the vector. An appropriate concentration of adenovirus would normally fall between $1.0 \times 10^{10} - 2.5 \times 10^{10}$ pfu/mL. The medium is infused into the lumen of the vessel for 30 minutes at room temperature to ensure efficient transfection. Thereafter, the vein is anastomosed as an end-to-end interpositional graft where needed.

In another embodiment, a pharmaceutical composition according to the invention can be employed for tissue reconstruction in, for example, the cardiovascular, gastrointestinal, genitourinary, or respiratory systems. The biocompatibility of the elastin-based compositions makes the compositions of the invention particularly useful in reconstructing segments of, for example, the common bile duct, a pancreatic duct, the esophagus, the urethra, the bladder, the uterus, an ovarian duct, and the like.

The present invention is further illustrated in the following examples, which are offered by way of illustration and are not intended to limit the invention in any manner.

EXAMPLE 1

ELN +/− and ELN −/− Mice

Materials and Methods

Construction of Targeting Vector

Two phage from a 1 FIX II library (Stratagene, La Jolla, Calif.) encompassing exon 1 and spanning a total of 26 kb were isolated, mapped and subcloned. A targeting vector was constructed using a 6.5 kb XbaI fragment as the 5' region of homology and a 4.2 kb BamHI-HindIII fragment as the 3' region of homology. Positive selection was provided by a 3.1 kb SacI-ClaI fragment containing the neomycin resistance gene under the control of the RNA polymerase II promoter. These fragments were cloned into the vector TK1-TK2A which provided two thymidine kinase genes for negative selection (Deng et al., 1993).

Generation of Mice

Culture, selection of embryonic stem cells, and screening of targeted clones were carried out as previously described (Mansour et al., 1988; Thomas and Capecchi, 1990; Lohler et al., 1984; Dietz and Pyeritz, 1995). The R1 embryonic stem cell line used was derived from strain 129/SV×129/SVJ. Clones were screened by Southern blot analysis of XbaI digested genomic DNA probed with a 3.0 kb HinDIII-XbaI fragment. Random integration events were excluded using a probe derived from the 3' region of homology. The homologous recombinant clones were injected into blastocysts of C57BL/6J and transferred into uteri of pseudopregnant C57BL/6J females. The resulting chimeric animals were backcrossed to C57BL/6J mice, and heterozygous mutants were identified by genomic Southern blotting of tail DNA. Heterozygous mice were mated for three generations with C57BL/6J mice and brother-sister matings were carried out to generate homozygous mutants.

Northern Analysis and In Situ Hybridization

Poly A(+) RNA was extracted from the visceral organs of the thorax from P0.5 mice using a Micro-FastTrack Kit (Invitrogen, Carlsbad, Calif.). RNA was electrophoresed on a 1.0% denaturing agarose gel, transferred to Hybond filter (Amersham, Arlington Heights, Ill.), and hybridized with a $^{32}$P-labeled 0.85 kb fragment of mouse ELN cDNA. Filters were rehybridized with a 1.5 kb fragment of human cardiac actin cDNA.

Paraffin-embedded cross-sections were hybridized with specific $^{35}$S-labeled antisense and sense ELN complementary RNA probes. Probes were synthesized from linearized templates using T3 and T7 RNA polymerases. Hybridization and washes were performed as described (Prosser et al., 1989). Sections were exposed to emulsion for several weeks and analyzed using bright- and dark-field microscopy.

Histological Examination

Mice were fixed overnight in either 4% paraformaldehyde or methyl Carnoys at 4° C. and embedded in paraffin. Transverse sections of the ascending and descending aortas were examined at the point at which the pulmonary artery crosses the ascending aorta posteriorly and bifurcates. Sections were stained with hematoxylin and eosin, Hart, and Masson-trichrome. Lamellar units and cell numbers were counted on two separate occasions by individuals blinded to the genotype. The statistical significance was calculated by comparison of the means using Student's t-test analysis.

Immunohistochemistry

Tissue samples were immunostained with a monoclonal antibody against smooth muscle a-actin (clone 1A4, 1:400, Sigma Chemical, St. Louis, Mo.), human von Willebrand factor antibody (1:1000, DAKO, Carpinteria, Calif.), or proliferating cell nuclear antigen (PCNA) monoclonal antibody (clone PC10, 3 mg/mL, Calbiochem, San Diego, Calif.).

Biotinylated donkey anti-rabbit antibody (RPN 1004, 1:2000, Amersham) was used as a secondary antibody for von Willebrand factor, and biotinylated goat anti-mouse $IgG_{2a}$ antibody (RPN 1181, 1:100, Amersham) was used as a secondary antibody for smooth muscle a-actin and PCNA. Sections immunostained for smooth muscle a-actin or von Willebrand factor were developed with 3-amino-9-ethylcarbazole chromagen (DAKO) and counterstained with Mayers hematoxylin (Sigma Chemical). Sections immunostained for PCNA were developed in 3,3'-diaminobenzidine chromagen (Vector Laboratories, Burlingame, Calif.) and counterstained with methyl green.

Vascular Extensibility

The ascending aorta from 5–6 month old mice was cannulated and mounted on the pressure myograph (Boyle, 1995). The vessel was transilluminated under an inverted microscope connected to a CCD camera, allowing the continuous recording of the outer diameter of the vessel. Intravascular pressure was increased from 75 to 175 mm Hg by steps of 25 mm Hg, and arterial diameter was recorded. Extensibility was calculated by the following formula using 100 mm Hg as an example; extensibility =[(diameter at 125 mm Hg–diameter at 75 mm Hg)/diameter at 75 mm Hg)]× 100. Statistical analysis was assessed by a four way ANOVA followed by Least Significance Difference test for post ANOVA paired comparisons.

Organ Culture

Ascending aortas were dissected from mouse embryos at E16.5 and washed in PBS. Aortas were cultured for 24 hours at 37° C. in 5% fetal bovine serum in DMEM. After 24 hours of culturing, each aorta was fixed in 1 mL methyl Carnoys fixative for 16 hours. ELN ++ and ELN –/– aortas were selected for processing and embedding in paraffin.

Electron Microscopy

Ascending thoracic aortas were dissected from mouse pups at birth following cardiac perfusion with 3% glutaraldehyde. Aortic segments were sequentially stained with osmium tetroxide, tannic acid and uranyl acetate, then dehydrated and embedded in Epon (Davis, 1995). Thin sections (60 nm) were counterstained with uranyl acetate and lead citrate and examined on a Jeol 1200 electron microscope.

Results

Targeted Disruption of Murine ELN

Figure 3:
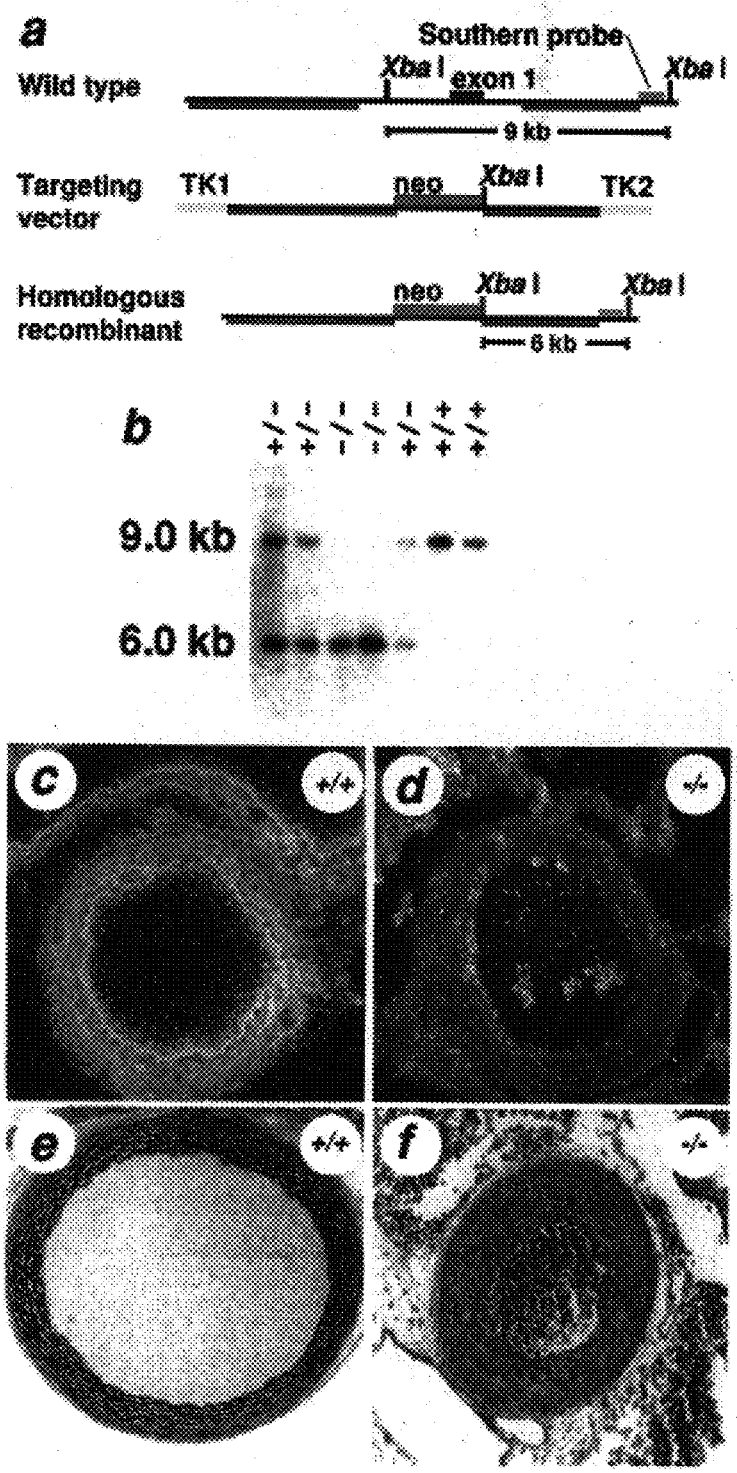
FIG. 3A is a diagram of the targeting vector designed to delete the promoter and exon 1 of the ELN gene. TK is thymidine kinase.
FIG. 3B shows a Southern blot analysis of tail DNA, digested with XbaI, from ELN +/+, ELN +/−, and ELN −/− mice. The 9-kb wild-type and 6-kb targeted XbaI fragments were identified using a probe outside the 3' region of homology.
FIGS. 3C and 3D show in situ hybridization of ELN +/+ (FIG. 3C) and ELN −/− (FIG. 3D) mice at E17.5 used to study ELN expression. Dark-field photomicrographs show the presence of silver grains in ELN +/+ mice and their absence in ELN −/− mice. The results demonstrate that no elastin mRNA is detected in ELN −/− mice.
FIGS. 3E and 3F show that Hart stain detected elastic fibers (stained dark brown) in ascending aortas from ELN +/+ mice (FIG. 3E) at birth (post partum 0.5 day). Elastin is organized into polymers that form concentric rings of elastic lamella around the arterial lumen. Each elastic lamella alternates with a ring of smooth muscle, forming a lamellar unit. There were no elastic fibers in ELN −/− mice (FIG. 3F).
Figure 4:
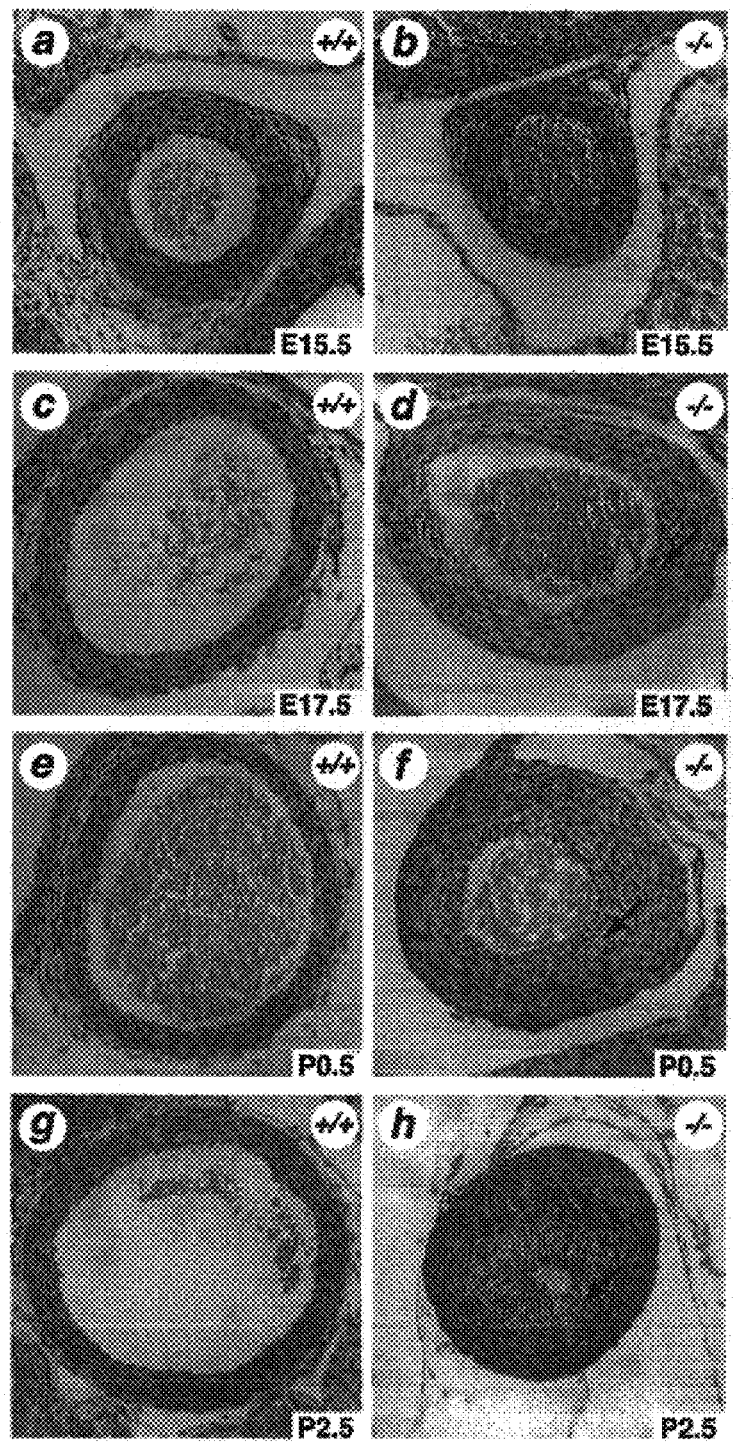
FIGS. 4A–H show the histology of different developmental stages in ELN +/+ and ELN −/− aortas. Cross-sections of ascending aortas (at the level of the pulmonary artery) stained with hematoxylin and eosin were examined at E15.5 (FIGS. 4A and 4B), E17.5 (FIGS. 4C and 4D), P0.5 (FIGS. 4E and 4F) and P2.5 (FIGS. 4G and 4H). No difference was noted at E15.5. Subsequent timepoints revealed subendothelial accumulation of cells in ELN −/− mice (arrows) and obliteration of the lumen by P2.5. All ELN −/− mice were dead by P4.5, presumably from the rapid obliteration of the aorta and other arteries. The ratios of lung weight to body weight and of heart weight to body weight in ELN −/− and ELN +/+ mice were comparable, suggesting that pulmonary edema was not the cause of death (n=8). There was no evidence of cardiac hypertrophy, dilatation or ischemia.
Figure 5:
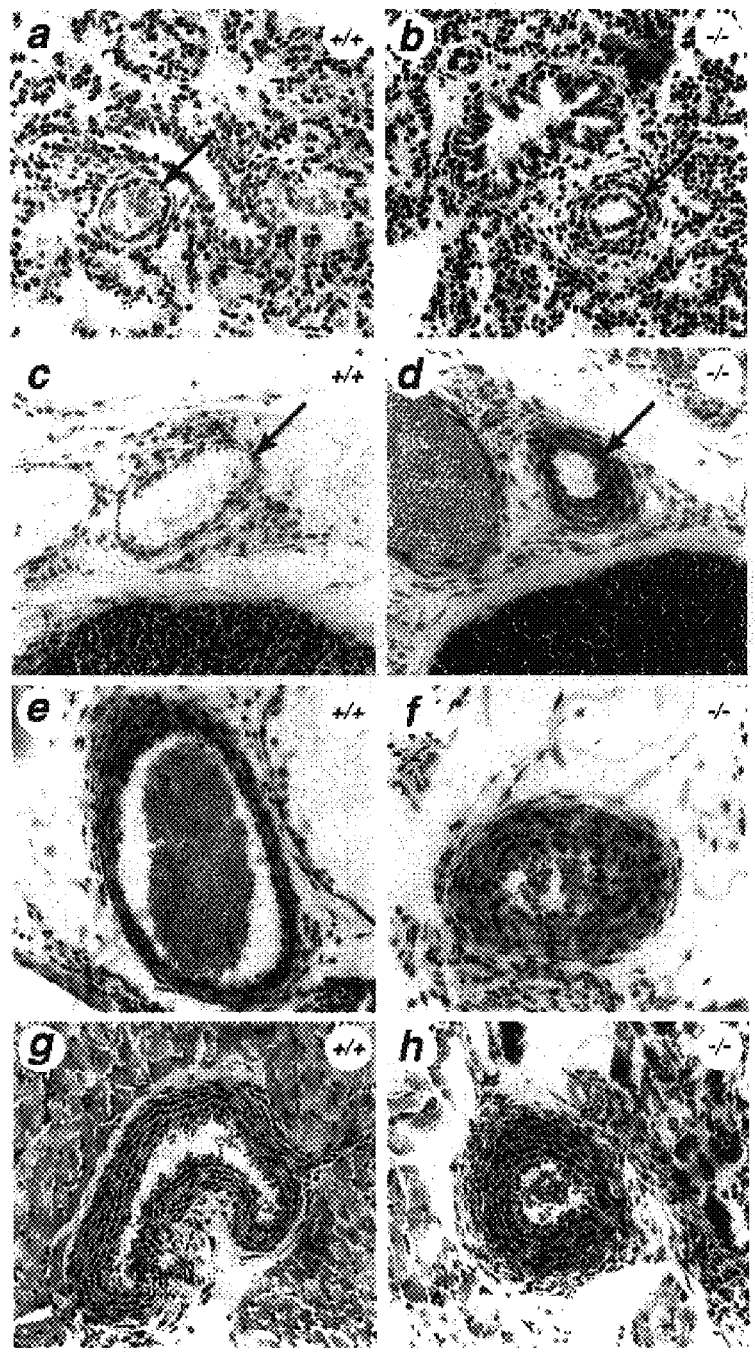
FIGS. 5A–H show the consequences of elastin deficiency in different arteries. Sections of pulmonary arterioles (arrow) at the level of a terminal bronchiole at P2.5 (FIGS. 5A and 5B), the internal mammary artery (arrow) at P2.5 (FIGS. 5C and 5D), a distal portion of the subclavian artery at P0.5 (FIGS. 5E and 5F), and the abdominal aorta at P0.5 (FIGS. 5G and 5H) were stained with hematoxylin and eosin and examined. There is increased cellularity and narrowing of the lumen for all of these ELN −/− arteries.

Murine genomic clones encoding elastin (ELN) were isolated from an SV/129 1 FIX II library using an ELN cDNA clone. A targeting vector was constructed to delete 4.0 kb of the promoter and exon 1, resulting in a null mutation (FIG. 3A). The vector was electroporated into R1 embryonic stem cells and homologous recombinants were isolated by positive-negative selection (Mansour et al., 1988). Three out of 160 clones were identified as homologous recombinants by Southern analysis (FIG. 3B). These three clones were microinjected into C57BL/6 blastocysts and implanted in pseudopregnant females (Thomas and Capecchi, 1990). All three independent cell lines generated chimeras that transmitted the null ELN allele. The resulting ELN +/– mice were mated to generate ELN –/– mice.

The disrupted ELN allele is a null as demonstrated by the absence of ELN mRNA and protein in ELN –/– mice (FIGS. 3C–F). Elastin expression during fetal development is largely confined to the vascular system and begins in the last third of gestation (Parks et al., 1993). In situ hybridization demonstrated the absence of ELN mRNA in the aorta of ELN –/– mice and its presence in ELN +/+ and ELN +/– mice (FIGS. 3C–D). Northern analysis showed an absence of ELN mRNA in ELN –/– mice at birth, (0.5 days post partum). Hart staining demonstrated the absence of elastin protein in ELN –/– mice (FIGS. 3E–F).

By contrast with ELN +/+ mice, Northern analysis of ELN +/– mice revealed a 47% decrease in ELN mRNA. To determine if the structure of elastic lamellae in ELN +/– mice was affected, aortic cross sections were examined by electron microscopy. Elastic lamellae in ELN +/– mice were approximately 50% thinner than those in ELN +/+ mice. These data indicate that elastic lamellae in ELN +/– mice are structurally abnormal, presumably due to reduced synthesis of elastin mRNA and protein during development.

Changes in Structure and Function of ELN +/– Aortas

ELN +/– mice were identical to ELN +/+ mice in gross appearance, behavior, and life expectancy (Table 1). To determine the effect of ELN hemizygosity on arterial structure, the vascular system was examined using light and electron microscopy. The ascending and descending aorta were examined at 5–14 months. It is generally believed that the number of lamellar units in an artery is fixed, species-specific and genetically determined (Katoh and Periasamy, 1996; Wolinsky and Glagov, 1967). However, aortas dissected from ELN +/– mice had additional lameilar units. Consistent with previous work (Wolinsky and Glagov, 1967; Davis, 1995), ELN +/+ aortas had 5.4±0.5 and 8.4±0.5 layers of elastic lamellae, respectively, in the descending and ascending aorta (Table 2). By contrast, cross sections of ELN +/– mice revealed an increase in the number of lamellar units to 7.3±0.6 and 10.5±0.5 layers, respectively (p<0.005). This represented an increase of 35% and 25% for the descending and ascending aorta of ELN +/– mice. There were no histological differences identified in the cardiac, pulmonary, gastrointestinal, renal, endocrine, musculoskeletal, or integumentary systems. These results indicate that ELN +/– mice develop aortas with an increased number of elastic lamellae.

To determine the physiological consequences of structural changes observed in ELN +/–mice, aortic diameter and extensibility were measured at varying intraluminal pressures. At a physiological pressure of 100 mm Hg, diameter and extensibility of ELN +/+ and ELN +/– mice were similar. At 125 mm Hg and above, however, the pressure-diameter curves diverged with a marked reduction in extensibility of ELN +/– aortas (p<0.05). These data indicate that ELN +/– mice maintain aortic diameter and extensibility at physiological pressure.

ELN +/− Mice Predict SVAS Pathology

SVAS is a human obstructive arterial disease that results from elastin hemizygosity (Ewart et al., 1993). To determine if developmental changes observed in ELN +/− mice were also present in SVAS, aortic segments from affected individuals were examined (n=2 for affected, n=3 for controls). Specifically, regions of the aorta that were free of discrete stenosis were studied. The number of lamellar units in controls was consistent with previous reports (Machii and Becker, 1997). By contrast, the aortic wall of individuals with SVAS was thicker and contained 2.5 fold more lamellar units (152±27.6 vs. 62±8.7, p<0.025). These data indicated that humans with ELN hemizygosity, like their murine counterpart, develop an increased number of aortic elastic lamellae.

TABLE 1

Life Expectancy of ELN +/+, ELN +/−, and ELN −/− Mice

|  | +/+ | +/− | −/− |
|---|---|---|---|
| Embryonic (E15.5–18.5) | 97 (28%) | 163 (48%) | 82 (24%) |
| Postnatal |  |  |  |
| P0.5 | 94 (29%) | 152 (46%) | 81 (25%) |
| P1.5 | 19 (24%) | 45 (57%) | 15 (19%) |
| P2.5 | 33 (26%) | 74 (59%) | 19 (15%) |
| P3.5 | 10 (48%) | 10 (48%) | 1 (4%) |
| >P3.5 | 65 (31%) | 140 (69%) | 0 (0%) |

Litters of mice were sacrificed at each timepoint and genotypes were tabulated. Percentages are calculated in the parenthesis. No ELN −/− mice were alive after P3.5.

TABLE 2

Number of Lamellar Units in ELN +/+ and ELN +/− Aortas

| Mouse ID | Genotype | Age | Ascending | Descending |
|---|---|---|---|---|
| BL6 | WT | 5 mo | 9 | 6 |
| 390-3 | WT | 12 mo | 8 | 5 |
| 390-10 | WT | 14 mo | 8 | 6 |
| 390-11 | WT | 14 mo | 8 | 5 |
| 1002-7 | WT | 4 mo | 9 | 6 |
| 1029-8 | WT | 5 mo | 8 | 5 |
| 1045-3 | WT | 5 mo | 9 | 5 |
|  |  | Average: | 8.4 ± 0.5 | 5.4 ± 0.5 |
| 390-6 | HET | 12 mo | 11 | 7 |
| 390-8 | HET | 14 mo | 11 | 7 |
| 390-9 | HET | 14 mo | 11 | 7 |
| 705-7 | HET | 7 mo | 11 | 8 |
| 720-2 | HET | 7 mo | 10 | 8 |
| 720-6 | HET | 7 mo | 10 | 6 |
| 1029-4 | HET | 6 mo | 11 | 8 |
| 1029-5 | HET | 6 mo | 10 | 7 |
| 1029-6 | HET | 5 mo | 10 | 7 |
| 1029-7 | HET | 5 mo | 10 | 7 |
| 1045-1 | HET | 6 mo | 11 | 7 |
| 1045-4 | HET | 6 mo | 10 | 8 |
|  |  | Average: | 10.5 ± 0.5 | 7.3 ± 0.6 |

Differences in number of lamellar units between ELN +/− mice and ELN +/+ mice were statistically significant with a p<0.005.

Arterial Occlusion in ELN −/− Mice

ELN −/− mice survived gestation but died by P4.5 (Table 1). To determine the consequences of elastin deficiency, a developmental survey was performed (FIGS. 4A–H). The histological appearance of ascending aortas from ELN −/− and ELN +/+ mice were indistinguishable through embryonic day 17.5 (E17.5). Beginning at E17.5, the outer and inner aortic diameter of the ELN −/− mice became progressively smaller. In ELN +/+ mice, by contrast, the aorta continued to expand. The diameter of the arterial wall in ELN −/− mice became progressively thicker after E17.5. This change was caused by the subendothelial accumulation of cells, a process that eventually obliterated the vascular lumen. Cell counts of the ascending aorta demonstrated a significant difference between ELN +/+ and ELN −/− mice at E17.5 (P<0.025; n=5). By P2.5 there were 76% more cells in aortic cross-sections of the ELN −/− aortas (P<0.005; n=5).

The aorta and other large, conduit arteries are often referred to as elastic arteries because of the high elastin content and the highly organized structure of elastic lamella (Bloom and Fawcett, 1975). In distributing or muscular arteries, however, the relative proportion of elastin declines and the structure of elastic fibers in the medium is less defined. To determine the consequences of elastin deficiency in different arteries, a pulmonary arteriole, the internal mammary artery, a distal portion of the subclavian artery, and the abdominal aorta in ELN +/+ and ELN −/− mice were examined (FIGS. 5A–H). Increased cellularity and reduced luminal diameter were observed in systemic and pulmonary arteries of all sizes, including distributing arteries and arterioles (including the descending thoracic aorta, pulmonary, brachiocephalic and carotid arteries) (FIGS. 5A–D). These data indicate that development of several different arteries is abnormal in mice lacking elastin.

Figure 6:
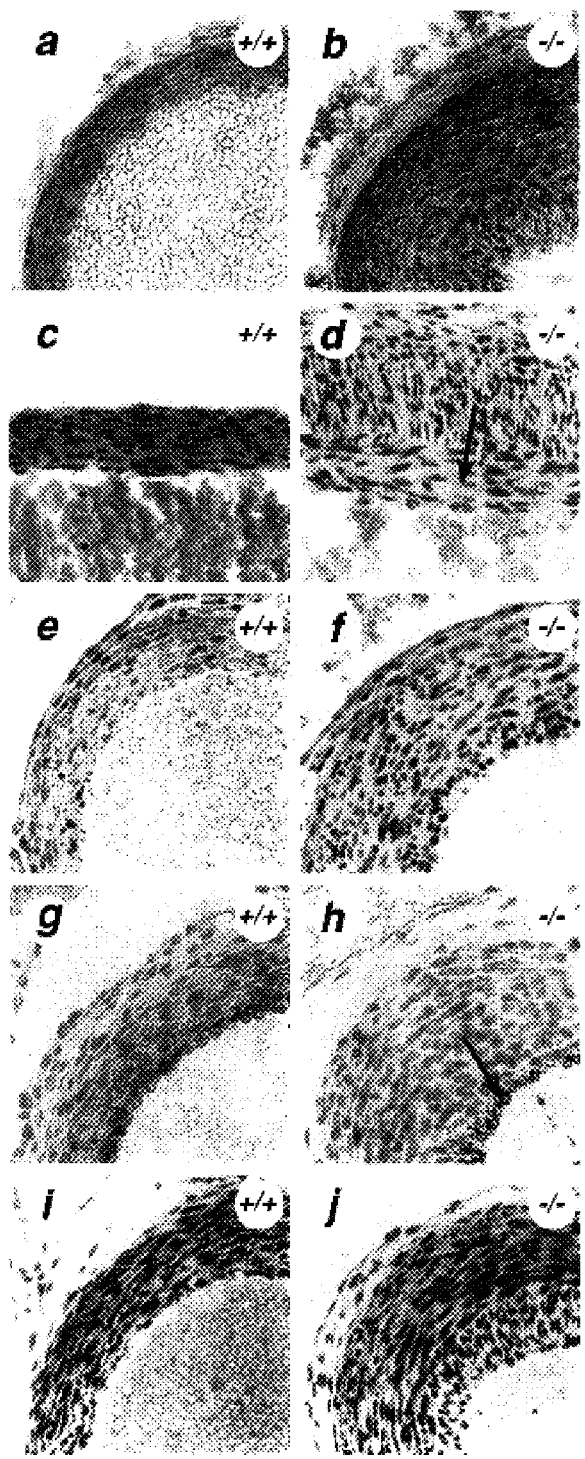
FIGS. 6A–J show the mechanism of luminal obliteration in ELN −/− mice.
Figure 7:
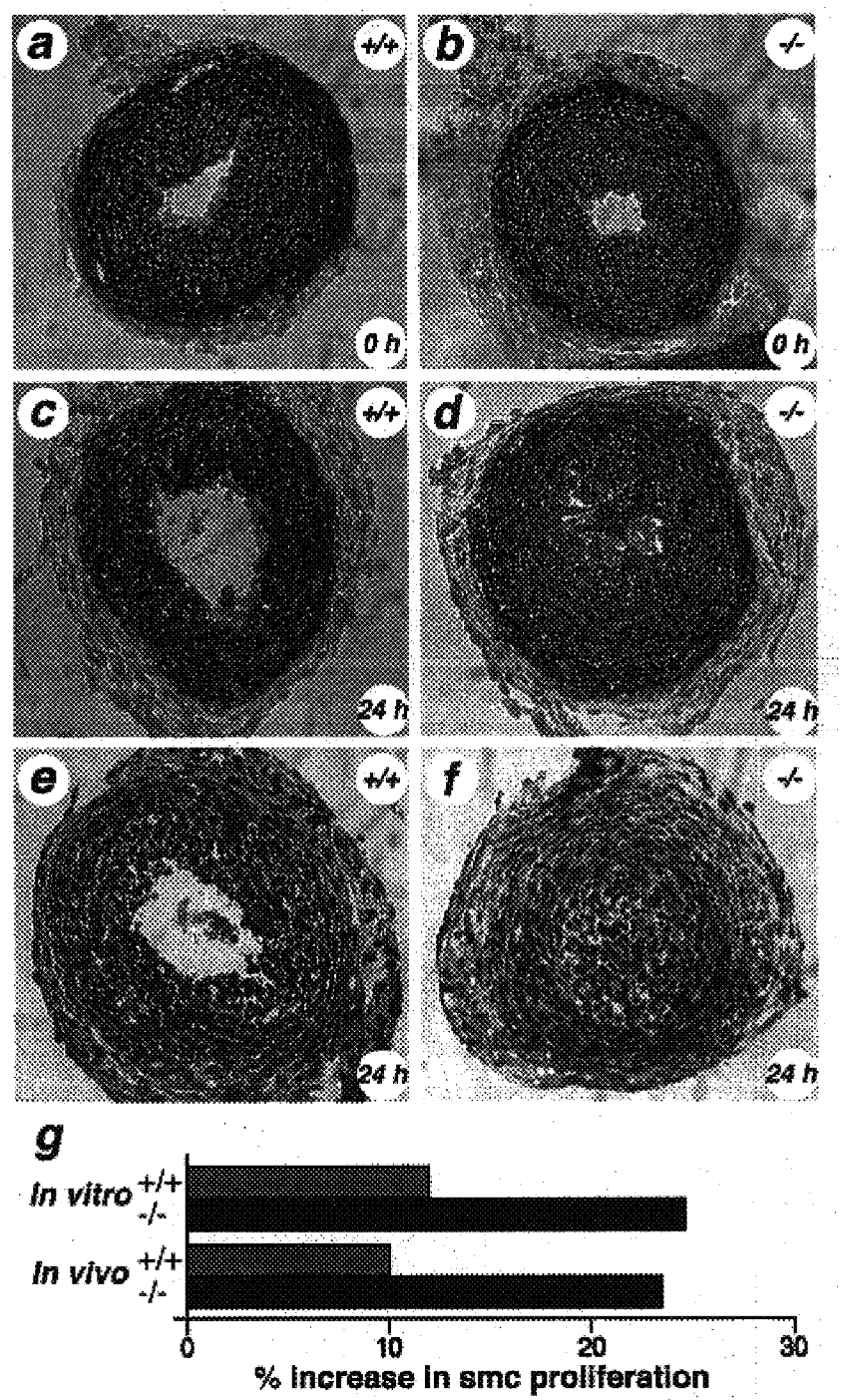
FIGS. 7A–G show the results of organ culture of ELN +/+ and ELN −/− aortas. Cross-sections of ELN +/+ (FIGS. 7A, 7C and 7E) and ELN −/− (FIGS. 7B, 7D and 7F) aortas with no incubation (FIGS. 7A and 7B) and 24 hours of incubation (FIGS. 7C, 7D, 7E and 7F) in Dulbecco's Minimum Essential Medium (DMEM) plus 5% fetal bovine serum. Sections in FIGS. 7A–7D were stained with antisera against smooth muscle a-actin, whereas sections in FIGS. 7E–7F were stained with hematoxylin and eosin.

The accumulating cells in aortic cross-sections of ELN −/− mice were morphologically distinct from smooth muscle in normal arteries. To determine the identity of these cells, aortic sections were immunostained with antisera against smooth muscle a-actin. The accumulating subendothelial cells present in ELN −/− aortas were positively stained (FIGS. 6A–B). Sagittal sections demonstrated that these cells were longitudinally oriented (FIGS. 6C–D). By contrast, smooth muscle cells in the media of control animals were circumferentially oriented. Thus, luminal obliteration in ELN −/− aortas results from subendothelial accumulation and reorientation of smooth muscle.

To examine the mechanism underlying smooth muscle accumulation in ELN −/− mice, aortic sections were stained with antisera to proliferating-cell nuclear antigen (PCNA; FIGS. 6E–F). At E17.5, the number of cells staining positive for PCNA was greater in ELN −/− mice than in ELN +/+ mice (88% vs. 35%). There was a gradient of staining, with subendothelial cells of ELN −/− aortas staining prominently. Intestinal sections were used as controls, confirming that PCNA was present in the crypts and absent in the villi. These experiments indicate that subendothelial proliferation of smooth muscle is a mechanism underlying the arterial pathology observed in ELN −/− mice.

Arterial Obliteration without Inflammation

The hallmark of obstructive arterial disease is subendothelial accumulation of smooth muscle cells (Ross, 1993; Schwartz et al., 1995). It is generally believed that recurrent endothelial injury, thrombosis, and inflammation induce this pathology (Ross, 1993). To determine if these processes were responsible for smooth muscle accumulation in ELN −/− aortas, histochemistry, immunohistochemistry, and electron microscopy were used to examine aortic sections. Sagittal and cross sections of aortas stained with antisera against smooth muscle a-actin revealed a single uninterrupted layer of unstained cells, the endothelium. The identity of these cells was further defined using antisera against von Willebrand factor (FIGS. 6G–H). No evidence of endothelial damage or disruption was observed. Microscopic examination of ELN –/– aortas stained with hematoxylin and eosin showed no evidence of inflammation, there was no ultrastructural evidence of rounding, protrusions, detachment or apoptosis of endothelial cells. Gross and histological examination of arteries revealed no evidence of thrombosis. These results, however, cannot exclude the possibility of endothelial dysfunction.

To determine whether inflammation was responsible for cellular pathology in ELN –/– aortae, sections were examined with hematoxylin and eosin (FIGS. 4A–H and 5A–H). There was no inflammation. Immunohistochemical analyses using the leukocyte-specific antibody Mac-3 also failed to show inflammation. Gross and histological examination of arteries showed no evidence of thrombosis. Because collagen is a ligand for integrin receptors and can modulate proliferation of smooth muscle, collagen levels were assessed using Masson trichrome (Koyama et al., 1996). No increase was found (FIGS. 6I–J). Electron micrographs confirmed the integrity of the endothelium, the lack of inflammation and normal distribution of other extracellular matrix proteins, including collagen. Thus, endothelial damage, thrombosis, inflammation; and fibrosis are not responsible for subendothelial accumulation of smooth muscle in ELN –/– mice and, therefore, are not necessary for inducing these pathological changes. Instead, ELN disruption is sufficient for initiating subendothelial accumulation and reorganization of smooth muscle.

Hypertension and hemodynamic stress are important mediators of obstructive arterial disease (Langille and Ojhu, 1997). To determine whether stress to the aortic walls was responsible for increased cell proliferation in ELN –/– aortas, aortic segments from ELN +/+ and ELN –/– embryos at E16.5 were incubated in organ culture (FIGS. 7A–G). In this system, there was no blood flow and no hemodynamic stress. Luminal obliteration by proliferating smooth-muscle cells occurred in ELN –/– mice within 24 hours, but not in ELN +/+ mice. The proliferative index for ELN aortas in organ culture was markedly increased compared with controls (27% vs. 14%; n=8). These indices were similar to those seen for ELN –/– and ELN +/+ aortas between E15.5 and E17.5 in vivo (25% versus 10%; n=5). Thus, blood flow, hemodynamic stress, gross endothelial damage, thrombosis, inflammation, and fibrosis are not responsible for subendothelial accumulation of smooth muscle in ELN –/– mice and therefore are not necessary for inducing these pathological changes. Instead, ELN disruption is enough to initiate accumulation and reorganization of smooth muscle. Therefore endothelial injury, thrombosis, and inflammation contribute to obstructive arterial pathology by disrupting elastin.

Physiological Regulation of Arterial Development

It was previously thought that the number of lamellar units in an arterial wall was fixed, species-specific and genetically determined (Katoh and Periasamy, 1996; Wolinsky and Glagov, 1967). The data described above are not consistent with this view. ELN +/– mice develop arteries with a marked increase in the number of lamellar units. Examination of arterial specimens obtained from individuals with SVAS, a human disorder caused by ELN hemizygosity, also revealed a dramatic increase in the number of elastic lamellae. Thus, the number of lamellar units in an arterial wall is not fixed or species-specific, but is modulated during development by elastin.

The mechanism underlying elastin's effect on lamellar development is unknown, but likely involves elastin content and wall stress. The increased number of lamellar units observed in ELN +/– mice was associated with reduced ELN mRNA and thinning of each elastic lamella. It is likely that a quantitative reduction in elastin during arterial development resulted in lamellae with reduced extensibility. These changes would lead to increased arterial wall stress, which is determined by arterial pressure and diameter and inversely proportional to the number of lamellar units and the tensile strength of each unit (Milnor, 1990). However, the extensibility and diameter of ELN +/– arteries were normal at physiological pressures. Thus, mice with abnormal elastic fibers maintain arterial extensibility by increasing the number of lamellar units during development. The alternative explanation, that elastin specifies the number of lamellar units by regulating gene expression during arterial development, is unlikely given the extracellular location of elastin. Also, physiological studies show that the relationship between wall stress and the number of elastic lamellae in an artery is remarkably constant despite enormous variation in arterial diameter and stress across species (Wolinsky and Glagov, 1967). These date indicate that the number of lamellar units in an arterial wall is modulated during development by the quantity of elastin and the physiological force of wall stress.

This work defines a novel pathology in a human obstructive arterial disease, supravalvular aortic stenosis (Perou, 1961; O'Connor et al., 1985). Because of arterial pathology in ELN +/– mice, apparently unaffected aortic sections from individuals with SVAS were reexamined to reveal a dramatic increase in the number of elastic lamellae. Thus, humans also respond to reduced elastin content by increasing the number of lamellar units during development. The change in humans (150% increase) was more dramatic than mice (25–35% increase), reflecting large differences in wall stress between these species (110,000 versus 7,800 dynes/cm). Extensibility in humans with SVAS cannot be examined, but progressive arterial pathology in affected individuals suggests that compensatory changes are inadequate, leading to discrete stenoses.

Elastin Defines a Fourth Stage of Vasculogenesis

The studies of ELN –/– mice define a novel stage of vasculogenesis. The results indicate a regulatory function for elastin and define a fourth stage of arterial development. In this fourth and final stage, the extracellular matrix matures, smooth muscle cells exit the cell cycle and become organized, and the artery stabilizes (Hanahan, 1997; Folkman and D'Amore, 1996; Schwartz et al., 1990; Owens, 1995). Arterial development in mice lacking elastin was indistinguishable from controls until E17.5, indicating that elastin has little or no effect on the first three stages of vasculogenesis (Folkman and D'Amore, 1996). During subsequent development, however, ELN –/– aortas became smaller and thicker, arterial diameter declined and the arterial lumen eventually obliterated. The cellular mechanism underlying these changes was subendothelial accumulation of arterial smooth muscle, a process that involved cell proliferation, migration, reorganization and reorientation. Thus, elastin is a molecular determinant of late arterial morphogenesis, stabilizing arterial structure by controlling proliferation and organization of vascular smooth muscle.

By contrast with the mechanism of pathology in ELN +/− mice, it is unlikely that wall stress has an important role in arterial obliteration in ELN −/− mice. As noted above, wall stress is directly proportional to arterial pressure and luminal diameter and inversely proportional to wall thickness. As wall thickness increases and luminal diameter decreases, wall stress declines and approaches zero. Thus wall stress cannot account for luminal obliteration in ELN −/− mice.

Elastin Disruption and Vascular Disease

Obstructive arterial diseases, such as atherosclerosis and restenosis, are the main cause of morbidity and mortality in industrialized nations (American Heart Association, 1996). Although much is known about vascular risk factors like hypercholesterolemia, hypertension, diabetes, and cigarette abuse, the pathogenic mechanism through which these diverse factors converge to give a common pathology is unknown (Schwartz et al., 1995; Gibbons and Dzau, 1996). The hallmark of obstructive arterial disease is subendothelial accumulation of smooth muscle cells, pathology that causes luminal narrowing and life-threatening sequelae (Gibbons and Dzau, 1996; Ross, 1993; Schwartz et al., 1995). Previous models have focused on endothelial injury, thrombosis and inflammation, processes that are thought to induce cellular accumulation through a complex interplay of cytokines and growth factors (Ross, 1993). By contrast with these models, there was no evidence of endothelial damage, thrombosis or inflammation in ELN −/− mice. Instead, disruption of ELN is sufficient for inducing smooth muscle proliferation and reorganization. Although disruption of extracellular matrix is a prominent feature of atherosclerosis, this process was not thought central to pathogenesis (Glagov et al., 1987; Galis et al., 1994). Therefore endothelial injury, thrombosis, inflammation, and other vascular risk factors induce subendothelial pathology by disrupting elastin and elastin is central to the pathogenesis of obstructive arterial disease.

EXAMPLE 2

Preparation of a Biologically Active Synthetic Peptide Derived from Elastin

A 42-amino acid peptide containing 7 repeats of a hexamer derived from the human elastin gene, VGVAPG-VGVAPG-VGVAPG-VGLAPG-VGVAPG-VGVAPG-VGVAPG (SEQ ID NO:2), was prepared by solid-phase peptide synthesis.

EXAMPLE 3

Method for Producing and Purifying Human Tropoelastin

A bacterial expression construct encoding an RGS6xHis-human elastin-cmyc fusion protein was constructed as follows. The starting material was a full-length human elastin cDNA encoding the following 712-amino acid protein:

```
MAGLTAAAPRPGVLLLLLSILHPSRPGGVPGAIPGGVPGGVFYPGAGLGALGGGALGPGGK

PLKPVPGGLAGAGLGAGLGAFPAVTFPGALVPGGVADAAAAYKAAKAGAGLGGVPGVG

GLGVSAGAVVPQPGAGVKPGKVPGVGLPGVYPGGVLPGARFPGVGVLPGVPTGAGVKPK

APGVGGAFAGIPGVGPFGGPQPGVPLGYPIKAPKLPGGYGLPYTTGKLPYGYGPGGVAGA

AGKAGYPTGTGVGPQAAAAAAAKAAAKFGAGAAGVLPGVGGAGVPGVPGAIPGIGGIAG

VGTPAAAAAAAAAAKAAKYGAAAGLVPGGPGFGPGVVGVPGAGVPGVGVPGAGIPVVP

GAGIPGAAVPGVVSPEAAAKAAAKAAKYGARPGVGVGGIPTYGVGAGGFPGFGVGVGGIP

GVAGVPGVGGVPGVGGVPGVGISPEAQAAAAAKAAKYGVGTPAAAAAKAAAKAAQFAL

LNLAGLVPGVGVAPGVGVAPGVGVAPGVGLAPGVGVAPGVGVAPGVGVAPGIGPGGVA

AAAKSAAKVAAKAQLRAAAGLGAGIPGLGVGVGVPGLGVGAGVPGLGVGAGVPGFGAV

PGALAAAKAAKYGAAVPGVLGGLGALGGVGIPGGVVGAGPAAAAAAAKAAAKAAQFGL

VGAAGLGGLGVGGLGVPGVGGLGGIPPAAAAKAAKYGVAARPGFGLSPIFPGGACLGKAC

GRKRK (SEQ ID NO:3)
```

Vector construction involved three steps:

1. A DNA fragment encoding the c-myc epitope was inserted in-frame at the 3'-end of the elastin coding sequence, and the coding sequence was flanked with restriction endonuclease sites to match the expression vector.

2. A DNA fragment encoding the RGS-6× His sequence was inserted in-frame at the 5'-end of the elastin-myc coding sequence while maintaining the 5' restriction site.

3. The completed fusion construct was inserted into a bacterial expression vector.

Step one was carried out in a single PCR reaction using the Expand High Fidelity® PCR System (Roche Molecular Biochemicals, Indianapolis, Ind.) and the following oligonucleotide primers:

Forward primer:

```
            M   A   G   L   T   A  (SEQ ID NO: 4)
5'-CTGCTGCTGCATATGGCGGGTCTGACGGCG-3' (SEQ ID NO: 5)
            NdeI
```

Reverse primer:

```
        Elastin                          C-Myc
  A  C  G  R  K  R  K  Q  K  L  I  S  E  E  D  L* (SEQ ID NO: 6)
3'-CGAACACCGGCCTTCTCTTTTGTCTTCGAGTAGTCGCTCCTCCTGGACACT
ACTTCTAGACGACGA-5' (SEQ ID NO: 7)
      BglII
```

The PCR product was blunt-end cloned into the EcoRV site (all restriction and cloning enzymes were from New England BioLabs, Inc., Beverly, Mass.) of pBluescript II SK + (Stratagene, La Jolla, Calif.). The sequence of the insert was verified by sequencing.

Step two was a single PCR reaction, as in step one, using the clone generated in step one as template. This reaction uses a reverse primer that is 3' of an Xcm I restriction site in the elastin coding sequence.

The PCR product was digested with Nde I and Xcm I, and this fragment was used to replace the 5'-end of the elastin-c-myc construct which had been removed by digestion with the same enzymes. The sequence of the completed fusion construct was verified by sequencing. The amino acid sequence of the complete 730-amino acid fusion construct was:

A: Bacterial Culture

1. Grow twenty-four 500 mL cultures to $OD_{600}=0.6$.

2. Induce with 0.4 mM (isopropyl β-D-thiogalactopyranoside) IPTG.

3. Express 4 hours and harvest by centrifugation.

4. Freeze pellets at −80° C.

B: Lysate Production

1. Resuspend pellet in lysis buffer: 7 M urea, 500 mM NaCl, 0.1% Triton X-100, 10 mM imidazole 10 mM Tris HCl, pH 7.2.

2. Lyse cells by vortexing and sonication.

3. Clarify lysate by centrifugation and filtration using Supor-200® membrane filters (Pall Gelman Laboratory, Ann Arbor, Mich.)

```
MRGSHHHHHHAGLTAAAPRPGVLLLLLSILHPSRPGGVPGAIPGGVPGGVFYPGAGLGAL

GGGALGPGGKPLKPVPGGLAGAGLGAGLGAFPAVTFPGALVPGGVADAAAAYKAAKAG

AGLGGVPGVGGLGVSAGAVVPQPGAGVKPGKVPGVGLPGVYPGGVLPGARFPGVGVLPG

VPTGAGVKPKAPGVGGAFAGIPGVGPFGGPQPGVPLGYPIKAPKLPGGYGLPYTTGKLPYG

YGPGGVAGAAGKAGYPTGTGVGPQAAAAAAAAKAAAKFGAGAAGVLPGVGGAGVPGVP

GAIPGIGGIAGVGTPAAAAAAAAAAKAAKYGAAAGLVPGGPGFGPGVVGVPGAGVPGVG

VPGAGIPVVPGAGIPGAAVPGVVSPEAAAKAAAKAAKYGARPGVGVGGIPTYGVGAGGFP

GFGVGVGGIPGVAGVPGVGGVPGVGGVPGVGISPEAQAAAAAKAAKYGVGTPAAAAAKA

AAKAAQFALLNLAGLVPGVGVAPGVGVAPGVGVAPGVGLAPGVGVAPGVGVAPGVGVA

PGIGPGGVAAAAKSAAKVAAKAQLRAAAGLGAGIPGLGVGVGVPGLGVGAGVPGLGVGA

GVPGFGAVPGALAAAKAAKYGAAVPGVLGGLGALGGVGIPGGVVGAGPAAAAAAAKAA

AKAAQFGLVGAAGLGGLGVGGLGVPGVGGLGGIPPAAAAKAAKYGVAARPGFGLSPIFPG

GACLGKACGRKRKQKLISEEDL (SEQ ID NO: 8)
```

For step three, the fusion construct was isolated from pBluescript II SK + by digesting with Nde I and Bgl II. The fusion construct was then cloned into pET-11a (Stratagene, La Jolla, Calif.) which had been cut with Nde I and BamH I.

The resulting expression vector was transformed into *E. coli* BL21(DE3) pLysS bacteria by electroporation, and human elastin was expressed according to the following protocol.

4. 12 liters of culture yields 1 liter of lysate.

C: Affinity Purification

Column: AP Biotech XK26 (Amersham Pharmacia, Piscataway, N.J.)

Matrix: Qiagen Ni-NTA Superflow Agarose, 50 mL bed volume (Qiagen, Inc., Chatsworth, Calif.)

1. Load column overnight at 1.8 mL/min. with 1.5 liters of lysate.

2. Wash at 6 mL/min. in Buffer A (4 M urea, 0.1% Triton X-100, 10 mM imidazole, 50 mM HEPES, pH 7.8).

3. Elute at 6 mL/min. using a solution of 25% of Buffer B (4 M urea, 0.1% Triton X-100, 1 M imidazole, 50 mM HEPES, pH 7.8) in Buffer A.

4. Collect a single 150 ml fraction.

D: Ion Exchange Purification

Column: AP Biotech HR 16/10 (Amersham Pharmacia, Piscataway, N.J.)

Matrix: AP Biotech Source 15S, 20 mL bed volume (Amersham Pharmacia, Piscataway, N.J.)

1. Load column at 6 mL/min. with 75 mL Ni column eluate.

2. Wash column at 6 mL/min. with: 4 M urea, 50 mM bicine, pH 8.0.

3. Elute at 6 mL/min. using a continuous gradient from 4 M urea, 200 mM glycine, pH 10.0, to 4M urea, 1 M NaCl, 200 mM glycine, pH 10.0.

4. Combine positive fractions, based on $OD_{250}$.

E: Concentration and Dialysis

1. Concentrate pooled fractions using Amicon 8200 stirred cell with PM30 membrane (Millipore Corp., Bedford, Mass.). Volume should be reduced 30-fold.

2. Dialyze against 3 changes of: 4 M urea, 50 mM bicine, pH 8.0. Elastin is stable for long-term storage in this solution. Dialysis is performed using Slide-A-Lyzer® 10 K dialysis cassettes (Pierce, Rockford, Ill.).

F: Dialysis for Use and Quantitation

Dialyze against 3 changes of one of the following physiological buffers: phosphate-buffered saline, Dulbecco's phosphate-buffered saline, Earle's balanced salt solution, Hank's balanced salt solution (tropoelastin will precipitate in pure water).

Results: The use of the above expression vector with this protocol enables the preparation of milligram to gram quantities of recombinant human tropoelastin.

EXAMPLE 4

Chemotactic Activity of Elastin Peptide and Tropoelastin

The elastin peptide described in Example 2 and recombinant tropoelastin prepared as described in Example 3 were assayed for chemotactic activity according to the following protocol. Any cells that migrate in response to elastin can be used to assay chemotactic activity. Examples include vascular smooth muscle cells and A2058 melanoma cells.

Day #1

Grow cells in 10 cm tissue culture plates. Approximately 400,000 cells/mL (200 μl/well of 24 well plate) are required for the assay.

Day #2

A. Growing cells to proper density:

1. Aspirate off media from each plate.

2. Rinse off each plate with 10 mL Dubecco's PBS (DPBS).

3. Add 5 mL of 5 mM EDTA with DPBS to detach cells from the plate; agitate cell culture medium if necessary to remove cells.

4. Once cells have come off plate, combine 5×5 mL cell suspension aliquots to yield 25 mL aliquots. Transfer each 25 mL aliquot to separate 50 mL centrifuge tubes.

5. Add 25 mL Dulbecco's Minimum Essential Medium, 1% bovine serum albumin (DMEM-1% BSA) to each 25 mL cell aliquot from #4.

6. Centrifuge 10 min. at 200 RCF.

7. Aspirate off supernatant.

8. Pool all cell pellets together in DMEM-1% BSA in a 50 mL centrifuge tube. The final volume of pooled pellets should be 15 mL.

9. Wash 3 times as follows: centrifuge 5 min. at 200 RCF; discard the supernatant and resuspend the pellet in 15 mL DMEM-1% BSA. Repeat 2 more times.

10. After the final wash, resuspend the pellet in 30 mL DMEM-1% BSA.

11. Incubate the suspension at 37° C. for 1 hr.

12. Filter the suspension using Steriltop® Cell Strainer (Millipore Corp., Bedford, Mass.) into 50 mL centrifuge tubes.

13. Wash the filter with 10 mL DMEM-1% BSA.

14. Count the cells. The density should be around 400,000 cells/mL. If not, repellet and resuspend in an appropriate volume of DMEM-1% BSA.

B. Experimental Set-Up

The experiment is performed in 24 well plates with chambers. Each measurement is repeated 4 times.

1. Test the following treatments for chemotactic activity:
   $10^{-8}$M elastin peptide
   $10^{-8}$M negative control peptide
   100 ng/ml tropoelastin 2. Add 700 μl treatment/well.

3. Test each chamber to ensure that it is not too porous (any chamber that begins to fill within 1–2 min. of being dipped into a treatment-filled well is too porous). Label each good chamber and place it over the appropriate well on the transwell plate.

4. Add 200 μl of 400,000 cells/mL cells to each chamber.

5. Incubate at 37° C. for 3 hr.

C. Staining the cells. Cells are stained using Diff Quick® Kit (Dade Ag, Duningen, Switzerland)

1. Prepare 100 mL of each of the following solutions in plastic beakers.
   PBS
   Zamboni's Fixative (Nature 20:174–175, 1967)
   Diff Quick® red
   Diff Quick® blue 2. Remove medium from each chamber.

3. Wash in PBS by holding chamber so the bottom is just below PBS. (Do not submerge the entire chamber in the PBS.)

4. Fix in Zamboni's—5 secs.

5. Dab with Q-tip to remove Zamboni's.

6. Stain in Diff Quick® red—5 secs.

7. Wash in PBS—S secs.

8. Stain in Diff Quick® blue 5 secs.

9. Wash in PBS

10. Dab with Q-tip.

11. Count the cells on the bottom of the well.

Figure 9:
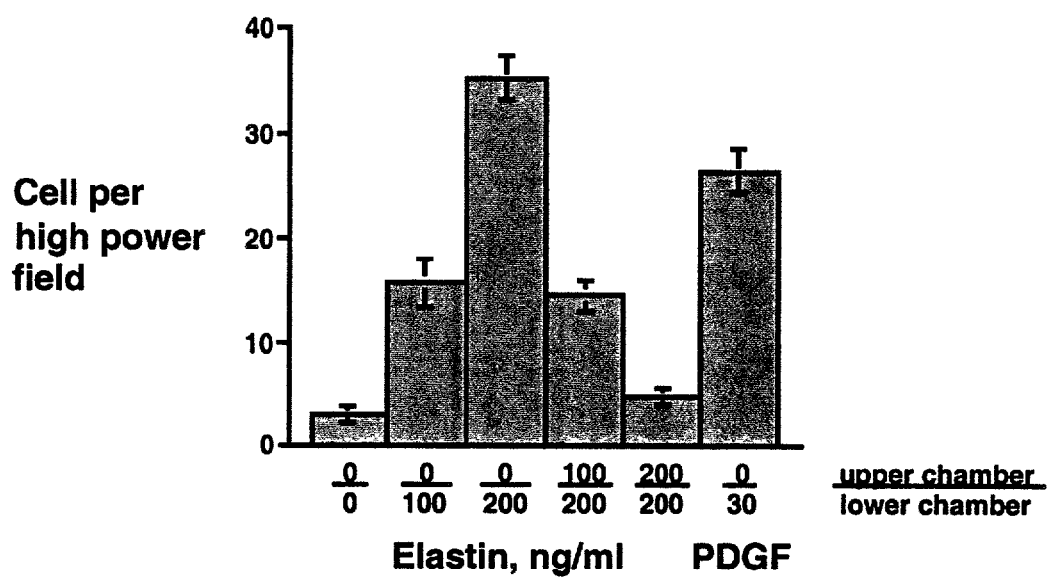
FIG. 9 shows that vascular smooth muscle cells migrate towards elastin in a dose-dependent manner. The concentrations of recombinant human tropoelastin (elastin) in the upper and lower chambers are plotted on the abscissa. The number of cells migrating is presented as cells per high power field according to convention. The positive control is platelet-derived growth factor (PDGF).
Figure 10:
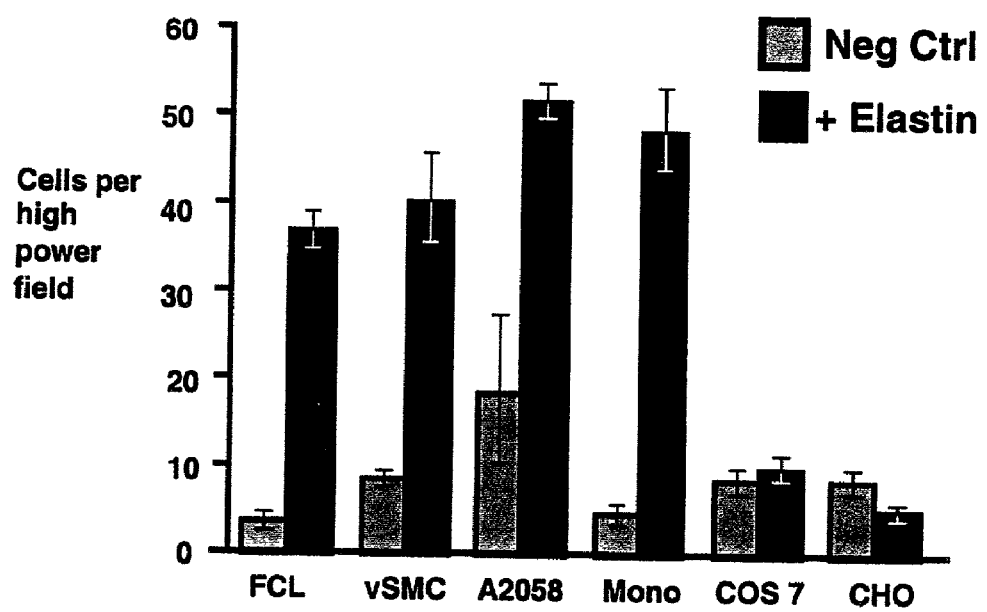
FIG. 10 demonstrates that the migration of vascular smooth muscle cells and other cell types occurs in a cell-specific manner. Fetal calf ligament (FCL) fibroblasts, murine vascular smooth muscle cells (vSMC), cells from a human melanoma cell line (A2058), and human monocytes (Mono) migrate toward recombinant human tropoelastin (Elastin). COS 7 and Chinese Hamster Ovary (CHO) cells do not respond to tropoelastin. Chemotaxis was measured in the absence of tropoelastin (hatched bar) and in the presence of 200 ng/ml of tropoelastin (black bars).
Figure 11:
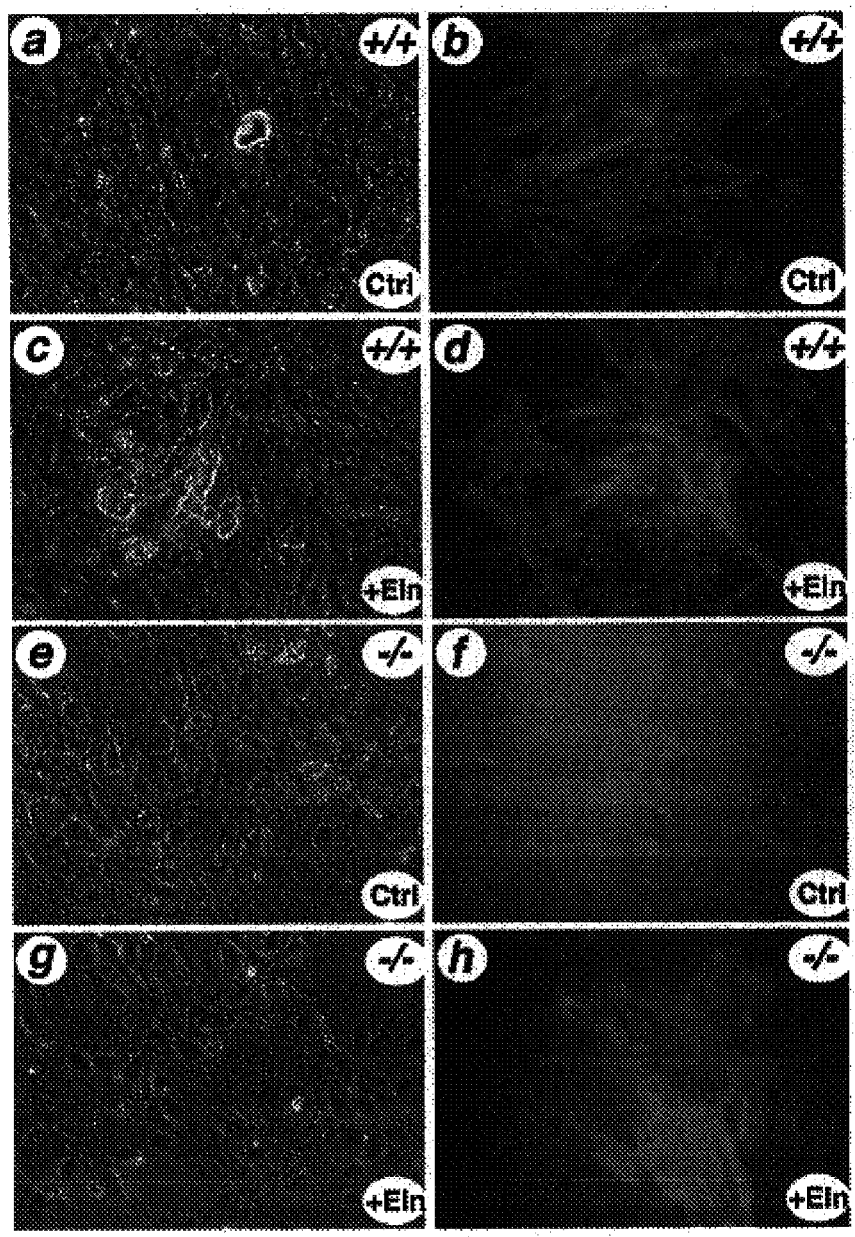
FIG. 11 illustrates immunofluorescence with alpha-smooth muscle cell actin antisera, revealing an absence of an organized contractile apparatus in ELN −/− vascular smooth muscle cell actin and its induction when ELN −/− cells are treated with recombinant tropoelastin.
Figure 12:
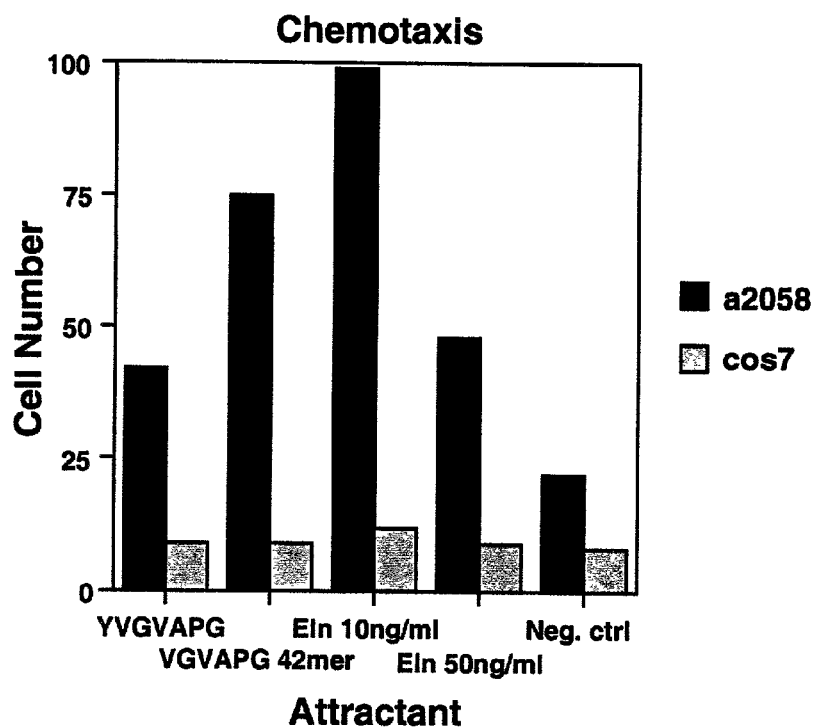
FIG. 12 demonstrates that human recombinant tropoelastin and the 42-amino acid peptide described in Example 2 are biologically active. Chemotaxis assays with cells known to migrate to elastin, A2058, and non-responsive cells, COS7, are shown. Both recombinant human tropoelastin (Eln) and the 42-amino acid peptide stimulate chemotaxis of A2058 cells, but not of COS 7 cells. The negative control is a hexapeptide, Val-Ser-Leu-Ser-Pro-Gly.
Figure 13:
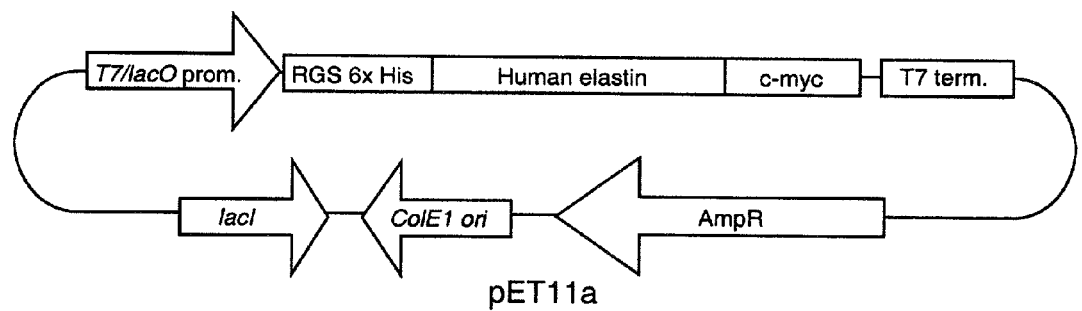
FIG. 13 shows an exemplary expression vector for recombinant human tropoelastin constructed from the Stratagene pET11a vector (Stratagene, La Jolla, Calif.). This vector encodes tropoelastin containing an engineered histidine tag at the amino-terminus and a c-myc epitope at the carboxyl-terminus to simplify purification and identification of the expressed protein. The expression of the cDNA is driven by a T7 promoter that is repressed by the lac operator (T7/lac o promoter) in the absence of isopropyl-β-galactopyranoside (IPTG). A T7 terminator sequence is included for efficient termination of expression. A lacI$^q$ gene provides adequate levels of lac I repressor to shut off T7 polymerase gene expression as well as T7 promoter transcription. This vector also contains a colE1 origin and an ampicillin resistance gene (AmpR).
Figure 14:
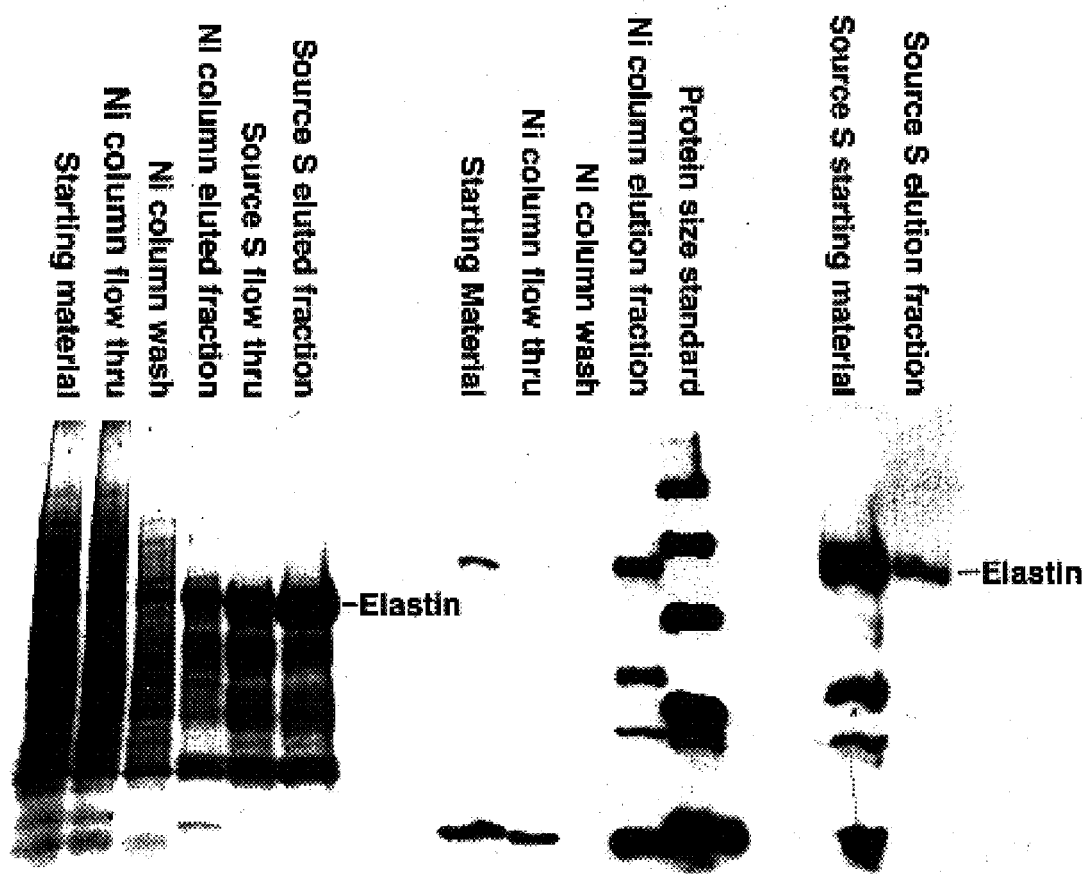
FIG. 14 illustrates the purity of the recombinant tropoelastin preparation of Example 3, as assessed by gel electrophoresis and western blotting. SDS-PAGE stained with SYPRO® Red. Western blotting with antisera recognizing the RGS-His$_6$ epitope confirms the identification of recombinant tropoelastin.
Figure 15:
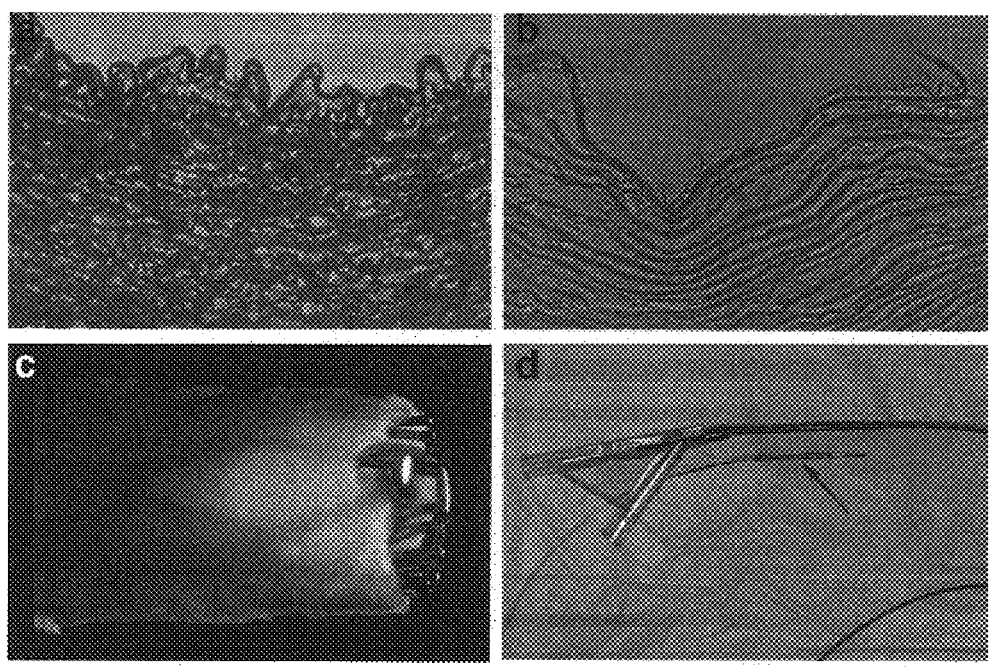
FIG. 15 shows a tubular elastin matrix and an elastin matrix-stent: a) Hart stain of an elastin matrix showing layers of elastic lamellae, b) Hematoxylin/eosin stain of an elastin matrix showing the absence of cellular material and other matrix components, c) Elastin tube fitted around an intravascular stent to form an elastin matrix-stent, and d) Elastin tube-stent loaded onto an angioplasty balloon prior to deployment into the coronary arteries of pigs.

Results:

The results of the chemotaxis assay are shown in FIG. 9, which indicates that the peptide is chemotactic and has comparable activity to recombinant human tropoelastin.

EXAMPLE 5

Ability of Elastin Peptide to Induce Differentiation of Vascular Smooth Muscle Cells Isolated from ELN –/– Mice The elastin peptide described in Example 2 and recombinant tropoelastin prepared as described in Example 3 were assayed for ability to induce differentiation of vascular smooth muscle cells isolated from ELN –/– mice according to the following protocol.

A. Seed cells in Amniomax C-100® medium containing Amniomax C-100® medium supplement at desired density in a 24-well plate (500 cells/well for statistical analysis).

B. After 15–18 hr. at 37° C., 5% $CO_2$, check cells for adherence.

1. Serum starve cells in DMEM for 3–4 hr.

2. Treat cells with $10^{-8}$M peptide or 1 μg/mL tropoelastin for 3 hr. Add tropoelastin/peptide directly to medium.

3. Remove medium and rinse cells 3 times with DPBS.

4. Fix in Zamboni's fixative for 10 min. at room temperature.

5. Rinse fixed cells with DPBS.

6. Permeabilize cells by treating with 0.2% Triton-100 in DPBS for 20 min. at room temperature.

7. Rinse permeabilized cells with DPBS.

8. Block by treating with 5% skim milk with DPBS for 30–45 min. in a 37° C. incubator.

9. Rinse 3 times with DPBS.

10. Add 200 μl rhodamine phalloidin (diluted 1:50 with DPBS) to each well.

11. Incubate 1 hr. in 37° C. incubator.

12. Rinse 3 time with DPBS.

13. Use the rhodamine filter of an immunofluorescence microscope to visualize stained cells.

Figure 8:
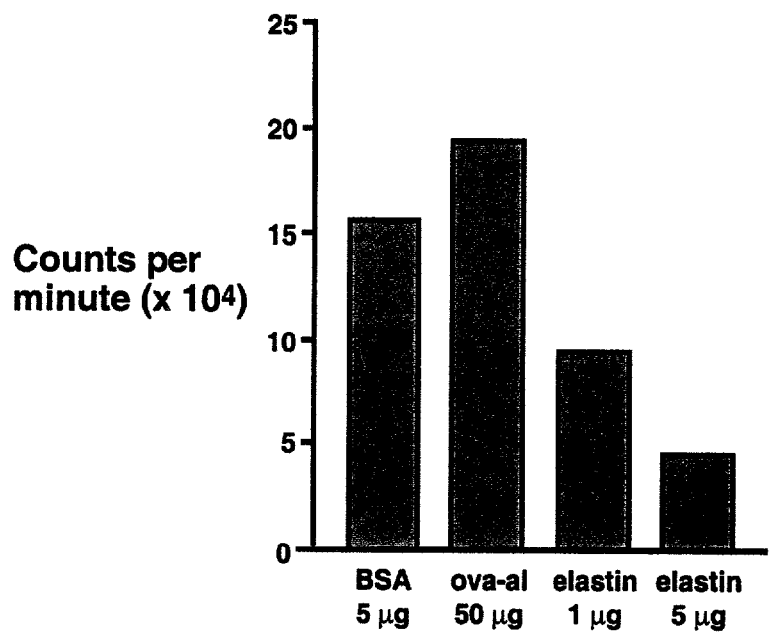
FIG. 8 shows that elastin binds to vascular smooth muscle cells in a specific manner. The amount of iodinated tropoelastin bound to cells after 1 hour at 22° C. is measured in the presence of excess recombinant human tropoelastin (elastin), ovalbumin (ova-al), and bovine serum albumen (BSA). Only tropoelastin reverses binding, indicating specific and reversible binding.

Results:

The results for tropoelastin are shown in FIG. 8. The contractile apparatus in ELN –/– vascular smooth muscle cells are poorly defined and almost undetectable. After treatment with recombinant tropoelastin, ELN –/– vascular smooth muscle cells show well-defined and well-organized actin staining of the contractile apparatus. Similar results are observed using the elastin peptides.

EXAMPLE 6

Elastin Peptide or Tropoelastin with a Biocompatible Support

Intravascular stents coated either with the elastin peptide described in Example 2 or tropoelastin prepared as described in Example 3 were produced as follows.

1. Mix 20 mg of elastin peptide or tropoelastin with 20 mg bovine serum albumin (BSA) in 40 μl of deionized water (peptide) or PBS (tropoelastin).

2. Crosslink mixture with 625% glutaraldehyde, pH 7.4 (Sigma, St. Louis, Mo.) for 4 to 30 minutes.

3. Coat stent (AVE/Medtronic, Santa Rosa, CA) with crosslinked mixture of peptide/tropoelastin. Surround stent and elastin-based composition with a tubular solid support molded to the appropriate diameter. This diameter is approximately 3.0 mm for an uncrimped intravascular stent. The solid support can be fabricated from metal, or plastic such as Teflon®.

4. Load apparatus onto 3.0 mm×20 mm balloon catheter (Predator, J&J/Cordis, New Brunswick, N.J.) and expand. This creates an elastin/BSA sheath around the intravascular stent.

5. Remove.

Results:

These elastin tubes supported by intravascular stents were inserted into the coronary arteries of pigs using standard angioplasty/stent insertion techniques. No acute thrombosis or rejection was been observed. The results indicate that elastin tubes supported by a biocompatible support are effective in preventing vascular restenosis.

EXAMPLE 7

Elastin Tubes Produced from Blood Vessels

Elastin tubes were produced from arteries as described below. This method can be used to isolate any blood vessel of the desired size and thickness from any vertebrate species in accordance with the size and thickness needed for the elastin matrix required.

1. Adult swine (40–60 kg) are euthanized according to institutional animal use protocol and carotid arteries are harvested through a single midline cervical incision using aseptic surgical technique. Carotid arterial segments are unbranched and average 3–4 mm in internal luminal diameter and between 8–10 cm in length. These vessels are rinsed in bacteriostatic saline and placed on ice until further treatment.

2. Place each vessel in a petri dish in fresh 0.1% Tween-100 in PBS. Under a dissecting microscope, remove the adventitia by making a superficial cut in the outer layer of each vessel and then pulling the adventitial layers off with forceps. Cut the distal portion of each vessel into two 3 cm segments.

3. Wash carotid segments in bacteriostatic saline for 15 minutes (3 changes of solution).

4. Incubate segments for 15–18 hr. at 37° C. with gentle agitation in a 1% SDS solution supplemented with 10 mg/L doxycycline and 5 mM EDTA.

5. Rinse SDS-treated segments 5 times in normal saline (0.9% NaCl).

6. Place segments in 5N KOH for 10 minutes at 60° C.

7. Rinse segments for 1 hour in normal saline (5 changes of solution).

8. Immerse segments in a collagenase solution (Collagenase D, 0.5 mg/ml in 0.9% NaCl, Roche, Inc.) for 1 hour at 37° C.

9. Rinse segments in ddH$_2$O for 1 hour (5 changes of solution).

10. Rinse segments in 70% EtOH for 1 hour (3 changes of solution).

11. Store elastin matrix in fresh 70% EtOH at ~4° C.

EXAMPLE 8

Elastin Matrices with Biocompatible Supports

Preparation of intravascular stents coated with elastin matrices prepared as described in Example 7 was begun approximately 3 hr. before vascular implantation. Aseptic technique was used throughout this procedure to ensure that the elastin matrix, intravascular stent, and the balloon catheter remained sterile.

1. Remove the elastin matrices from storage (70% EtOH, ~4° C.) and rehydrate in bacteriostatic normal saline for 30 minutes (3 changes of solution).

2. Treat the elastin matrices with heparinized normal saline (10,000 U/ml heparin; Elkins-Sinn, Inc., Cherry Hills, N.J.) for 30 min. (2 changes of solution).

3. Fit the heparinized elastin matrices onto a 3.5 mm×16 mm stent (Medtronic/AVE, Santa Rosa, CA) that is loaded onto an angioplasty balloon (Predator, J&J/Cordis, New Brunswick, N.J.). Cut excess elastin matrix away from the borders of the stent using a dissecting microscope.

4. Each balloon/intravascular stent/elastin matrix assembly is placed into a sterile vacuum flask and dried under vacuum (10 mm Hg) until secure, but not completely dry (approximately 1 hr.).

5. Insert each balloon/intravascular stent/elastin matrix assembly into a #7 French catheter (Cook Cardiology, Bloomington, Ind.) for implantation.

Results:

These elastin matrix stents have been placed in the coronary arteries of pigs. No acute thrombosis or rejection has been observed. The results indicate that these elastin matrix stents are effective in preventing vascular restenosis.

The publications and other materials used herein to illuminate the background of the invention or provide additional details respecting the practice, are incorporated by reference, and for convenience are respectively grouped in the appended List of Publications.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art that are within the spirit of the invention and the scope of the appended claims.

LIST OF PUBLICATIONS

Adams J C and Watt F M (1993). Development 117: 1183–1198.
American Heart Association (1996). Heart and Stroke Facts: 1996 Statistical Supplement (American Heart Association, Dallas, Tex.)
Beck L and D'Amore P A (1997). FASEB J. 11:365–373.
Bloom W and Fawcett D (1975). *A Textbook of Histology* 10th edn, pp. 398–402 (Saunders, Philadelphia).
Boyle W A and Maher G M (1995). Anesthesiology 82:221–235.
Carmeliet P, et al. (1996). Nature 380:435–439.
Curran M, et al. (1993). Cell 73:159–168.
Davis E C (1993). Lab. Invest. 68:89–99.
Davis E C (1995). J. Histochem. Cytochem. 43:1115–1123.
Deng C, et al. (1993). Mol. Cell. Biol. 13:2134–2140.
Dietz H C and Pyeritz R E (1995). Hum. Mol. Genet. 4:1799–1809.
Ewart A K, et al. (1993). Nat. Genet. 5:11–16.
Ferrara N, et al. (1996). Nature 380:439–442.
Folkman J and D'Amore P A (1996). Cell 87:1153–1155.
Fong G-H, et al. (1995). Nature 376:66–70.
Galis Z S, et al. (1994). J. Clin. Invest. 94:2493–2503.
Gardner H, et al. (1996). Dev. Biol. 175:301–313.
George E L, et al. (1993). Development 119:1079–1091.
Gibbons G H and Dzau V J (1996). Science 272:689–693.
Glagov S, et al. (1987). N. Engl. J. Med. 316:1371–1375.
Glukhova M A, et al. (1991). Am. J. Physiol. 261:78–80.
Gumbiner B M (1996). Cell 84:345–357.
Hanahan D (1997). Science 277:48–50.
Hynes R O (1992). Cell 69:11–25.
Hynes R O (1994). Curr. Opin. Genet. Dev. 4:569–574.
Katoh Y and Periasarny M (1996). Trends Cardiovasc. Med. 6:100–106.
Koyama H, et al. (1996). Cell 87:1069–1078.
Langille B C and Ojhu M (1997). Trends Cardiovasc. Med. 7:111–118.
Lindahl P, et al. (1997). Science 277:242–245.
Lohler J, et al. (1984). Cell 38:597–607.
Machii M and Becker A E (1997). Ann. Thorac. Surg. 64:511–515.
Mansour S L, et al. (1988). Nature 336:348–352.
Mecham R P and Hinek A (1996). In *The Laminins* (P. Elblom and R. Timpl, eds.; Harwood Academic Publishers).
Milnor W R (1990). In *Principles of Hemodynamics in Cardiovascular Physiology*, Oxford University Press, pp. 184–186.
O'Connor W N, et al. (1985). Arch. Pathol. Lab. Med. 109:179–185.
Owens G K (1995). Physiol. Rev. 75:487–517.
Parks W C, et al. (1993). Advances in Molecular and Cell Biology 6:133–182 (Kleinman H K, ed.; JAI, Greenwich).
Perou M (1961). Arch. Path. 71:113–126.
Prosser I W, et al. (1989). Am. J. Pathol. 135:1073–1088.
*Remington's Pharmaceutical Sciences,* 18th Ed. (1990, Mack Publishing Co., Easton, Pa.).
Ross R (1993). Nature 362:801–809.
Saga Y, et al. (1992). Genes Dev. 6:1821–1831.
Sato T N, et al. (1995). Nature 376:70–74.
Schwartz S M, et al. (1990). Physiol. Rev. 70:1177–1209.
Schwartz S M, et al. (1995). Circ. Res. 77:445–465.
Senior R M, et al. (1984). J. Cell Biol. 99:870–874.
Shalaby F, et al. (1995). Nature 376:62–66.
Suri C, et al. (1996). Cell 87:1171–1180.

Terpin T and Roach M R (1987). Can. J. Physiol. Pharmacol. 65:395–400.
Thomas K R and Capecchi M R (1990). Nature 346: 847–850.
Thompson R W (1996). Curr. Opin. Cardiol. 11:504–518.
Wolinsky H and Glagov S (1967). Circ. Res. 20:99–111.
Yang J T, et al. (1993). Development 119:1093–1105.
Yang J T, et al. (1995). Development 121:549–560.
Zheng X, et al. (1995). Proc. Natl. Acad. Sci. USA 92:12426–12430.
U.S. Pat. No. 5,550,050

WO 90/07936
WO 92/19195
WO 94/25503
WO 95/01203
WO 95/05452
WO 96/02286
WO 96/02646
WO 96/40871
WO 96/40959
WO 97/12635
EP 425,731A

What is claimed is:

1. A pharmaceutical composition that provides an elastin-based composition for localized delivery in vivo, said elastin-based composition consisting of a polypeptide, wherein said polypeptide consists of (i) an amino acid sequence at least 95% identical to SEQ ID NO: 3, (ii) an amino acid sequence represented by SEQ ID NO: 2, or (iii) a peptide fragment of six repeats of the hexameric sequence represented by SEQ ID NO: 1, wherein said elastin-based composition is attached to a biocompatible support or dissolved in a biocompatible matrix and has one or more biological activities selected from the group consisting of:
   a) inhibiting the proliferation of smooth muscle cells in vivo;
   b) stimulating the differentiation of smooth muscle cells in vivo;
   c) regulating the migration of smooth muscle cells in vivo; and
   d) binding to smooth muscle cells, and
wherein said elastin-based composition has an IC50/EC50 for at least one of said biological activities that is less than or equal to $10^{-3}$.

2. The pharmaceutical composition of claim 1 wherein said elastin-based composition is soluble and has an IC50/EC50 for each of said one or more biological activities that is less than or approximately equal to $10^{-3}$.

3. The composition of claim 1 or 2 wherein said IC50/EC50 is greater than $10^{-15}$.

4. The composition of claim 1 wherein said pharmaceutical composition provides a dose of said elastin-based composition equivalent to $10^{-8}$ M of a peptide having the amino acid sequence of SEQ ID NO:2 at said target site.

5. The composition of claim 1 wherein said elastin-based composition comprises a recombinant polypeptide.

6. The composition of claim 1 wherein said elastin-based composition comprises a synthetic peptide.

7. The composition of claim 6 wherein said synthetic peptide consists of six repeats of the hexameric sequence Val-Gly-Val-Ala-Pro-Gly (SEQ ID NO: 1).

8. The composition of claim 6 wherein said synthetic peptide consists of the amino acid sequence represented by SEQ ID NO: 2.

9. The composition of claim 1, wherein said elastin-based composition is crosslinked, precipitated, or coacervated.

10. The composition of claim 1 wherein said elastin-based composition comprises an elastin matrix produced from a blood vessel.

11. The composition of claim 1 wherein said elastin-based composition is attached to a biocompatible support or biocompatible matrix.

12. The composition of claim 11 wherein said biocompatible support or biocompatible matrix comprises a tube.

13. The composition of claim 12 wherein said elastin-based composition is attached to an outer surface of said tube and additionally comprises a sheath encircling said tube.

14. The pharmaceutical composition of claim 1, wherein said elastin-based composition is derivatized by linkage to one or more additional chemical groups for promoting sustained release.

15. A pharmaceutical composition that provides an elastin-based composition, said elastin-based composition consisting of a polypeptide, wherein said polypeptide consists of (i) an amino acid sequence identical to SEQ ID NO: 3, (ii) an amino acid sequence identical to SEQ ID NO: 2, or (iii) a peptide fragment of six repeats of the hexameric sequence represented by SEQ ID NO: 1, wherein said elastin-based composition is attached to a biocompatible support or dissolved in a biocompatible matrix and has one or more biological activities selected from the group consisting of:
   a) inhibiting the proliferation of smooth muscle cells;
   b) stimulating the differentiation of smooth muscle cells;
   c) regulating the migration of smooth muscle cells; and
   d) binding to smooth muscle cells, and
wherein said elastin-based composition has an IC50/EC50 for at least one of said biological activities that is less than or equal to $10^{-3}$.

16. The composition of claim 15, wherein said polypeptide consists of an amino acid sequence identical to SEQ ID NO: 3.

17. A method for prophylaxis of restenosis, comprising direct delivery of the pharmaceutical composition of claim 16 to a target site of diminished capacity to regulate smooth muscle cell function, wherein said direct delivery to said target site of diminished capacity to regulate smooth muscle cell function prevents restenosis.

18. The method of claim 17 wherein said IC50/EC50 is greater than about $10^{-15}$.

19. The method of claim 17 wherein said pharmaceutical composition provides a dose of said elastin-based composition equivalent to $10^{-8}$ M of a peptide having the amino acid sequence of SEQ ID NO:2 at said target site.

20. The method of claim 17 wherein said elastin-based composition is crosslinked, precipitated, or coacervated.

21. The method of claim 17 wherein said target site is located in the cardiovascular system and is suspected or known to be at risk for restenosis.

22. The method of claim 17 wherein delivery comprises intravascular delivery of said elastin-based composition directly to a vascular site.

23. The method of claim 17 wherein said elastin-based composition is delivered to and maintained at said site.

24. The composition of claim 15, wherein said polypeptide consists of an amino acid sequence identical to SEQ ID NO: 2.

25. A method for prophylaxis of restenosis, comprising direct delivery of the pharmaceutical composition of claim 24 to a target site of diminished capacity to regulate smooth muscle cell function, wherein said direct delivery to said target site of diminished capacity to regulate smooth muscle cell function prevents restenosis.

26. The method of claim 17 or 25 wherein said elastin-based composition comprises a recombinant polypeptide.

27. The method of claim 17 or 25 wherein said elastin-based composition comprises an elastin matrix produced from a blood vessel.

28. The method of claim 17 or 25, wherein said biocompatible support is a stent.

29. The method of claim 28 wherein said biocompatible support or biocompatible matrix comprises a tube.

30. The composition of claim 15, wherein said polypeptide consists of a peptide fragment of six repeats of the hexameric sequence represented in SEQ ID NO: 1.

31. The composition of claim 15, wherein said elastin-based composition is attached to a biocompatible support.

32. The composition of any of claim 1, 7, 8, or 15, where said elastin-based composition is dissolved or suspended within a biocompatible polymer matrix, which matrix permits diffusion of the elastin-based composition, to form a sustained-release composition.

33. The composition of claim 32, wherein the biocompatible polymer matrix is selected from the group consisting of polyester, a polylactide, degradable lactic acid-glycolic acid copolymers, and poly-D-(−) hydroxybutyric acid.

34. The composition of claim 32, wherein the biocompatible polymer matrix is formulated for coating an implantable medical device.

35. The composition of claim 32, wherein the biocompatible polymer matrix is formulated for coating a stent.

* * * * *

SEQUENCE LISTING

```
<160> NUMBER OF SEQ ID NOS: 8

<210> SEQ ID NO 1
<211> LENGTH: 6
<212> TYPE: PRT
<213> ORGANISM: Homo sapiens

<400> SEQUENCE: 1

Val Gly Val Ala Pro Gly
 1               5

<210> SEQ ID NO 2
<211> LENGTH: 42
<212> TYPE: PRT
<213> ORGANISM: Artificial Sequence
<220> FEATURE:
<223> OTHER INFORMATION: Synthetic

<400> SEQUENCE: 2

Val Gly Val Ala Pro Gly Val Gly Val Ala Pro Gly Val Gly Val Ala
 1               5                  10                  15

Pro Gly Val Gly Leu Ala Pro Gly Val Gly Val Ala Pro Gly Val Gly
             20                  25                  30

Val Ala Pro Gly Val Gly Val Ala Pro Gly
         35                  40

<210> SEQ ID NO 3
<211> LENGTH: 712
<212> TYPE: PRT
<213> ORGANISM: Homo sapiens

<400> SEQUENCE: 3

Met Ala Gly Leu Thr Ala Ala Ala Pro Arg Pro Gly Val Leu Leu Leu
 1               5                  10                  15

Leu Leu Ser Ile Leu His Pro Ser Arg Pro Gly Gly Val Pro Gly Ala
             20                  25                  30

Ile Pro Gly Gly Val Pro Gly Gly Val Phe Tyr Pro Gly Ala Gly Leu
         35                  40                  45

Gly Ala Leu Gly Gly Gly Ala Leu Gly Pro Gly Gly Lys Pro Leu Lys
     50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                 85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
```

-continued

```
            115                 120                 125
Val Pro Gln Pro Gly Ala Gly Val Lys Pro Gly Lys Val Pro Gly Val
        130                 135                 140
Gly Leu Pro Gly Val Tyr Pro Gly Gly Val Leu Pro Gly Ala Arg Phe
145                 150                 155                 160
Pro Gly Val Gly Val Leu Pro Gly Val Pro Thr Gly Ala Gly Val Lys
                165                 170                 175
Pro Lys Ala Pro Gly Val Gly Ala Phe Ala Gly Ile Pro Gly Val
            180                 185                 190
Gly Pro Phe Gly Gly Pro Gln Pro Gly Val Pro Leu Gly Tyr Pro Ile
        195                 200                 205
Lys Ala Pro Lys Leu Pro Gly Gly Tyr Gly Leu Pro Tyr Thr Thr Gly
        210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
                245                 250                 255
Ala Ala Ala Ala Lys Ala Ala Lys Phe Gly Ala Gly Ala Ala Gly
            260                 265                 270
Val Leu Pro Gly Val Gly Gly Ala Gly Val Pro Gly Val Pro Gly Ala
        275                 280                 285
Ile Pro Gly Ile Gly Gly Ile Ala Gly Val Gly Thr Pro Ala Ala Ala
        290                 295                 300
Ala Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                325                 330                 335
Pro Gly Ala Gly Val Pro Gly Val Gly Val Pro Gly Ala Gly Ile Pro
            340                 345                 350
Val Val Pro Gly Ala Gly Ile Pro Gly Ala Ala Val Pro Gly Val Val
        355                 360                 365
Ser Pro Glu Ala Ala Ala Lys Ala Ala Ala Lys Ala Ala Lys Tyr Gly
        370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Ile Pro Gly
                405                 410                 415
Val Ala Gly Val Pro Gly Val Gly Val Pro Gly Val Gly Gly Val
            420                 425                 430
Pro Gly Val Gly Ile Ser Pro Glu Ala Gln Ala Ala Ala Ala Lys
        435                 440                 445
Ala Ala Lys Tyr Gly Val Gly Thr Pro Ala Ala Ala Ala Lys Ala
        450                 455                 460
Ala Ala Lys Ala Ala Gln Phe Ala Leu Leu Asn Leu Ala Gly Leu Val
465                 470                 475                 480
Pro Gly Val Gly Val Ala Pro Gly Val Gly Val Ala Pro Gly Val Gly
                485                 490                 495
Val Ala Pro Gly Val Gly Leu Ala Pro Gly Val Gly Val Ala Pro Gly
            500                 505                 510
Val Gly Val Ala Pro Gly Val Gly Val Ala Pro Gly Ile Gly Pro Gly
        515                 520                 525
Gly Val Ala Ala Ala Ala Lys Ser Ala Ala Lys Val Ala Ala Lys Ala
        530                 535                 540
```

```
Gln Leu Arg Ala Ala Ala Gly Leu Gly Ala Gly Ile Pro Gly Leu Gly
545                 550                 555                 560

Val Gly Val Gly Val Pro Gly Leu Gly Val Gly Ala Gly Val Pro Gly
                565                 570                 575

Leu Gly Val Gly Ala Gly Val Pro Gly Phe Gly Ala Val Pro Gly Ala
            580                 585                 590

Leu Ala Ala Ala Lys Ala Ala Lys Tyr Gly Ala Ala Val Pro Gly Val
        595                 600                 605

Leu Gly Gly Leu Gly Ala Leu Gly Gly Val Ile Pro Gly Gly Val
    610                 615                 620

Val Gly Ala Gly Pro Ala Ala Ala Ala Ala Lys Ala Ala Ala
625                 630                 635                 640

Lys Ala Ala Gln Phe Gly Leu Val Gly Ala Ala Gly Leu Gly Gly Leu
                645                 650                 655

Gly Val Gly Gly Leu Gly Val Pro Gly Val Gly Leu Gly Gly Ile
                660                 665                 670

Pro Pro Ala Ala Ala Lys Ala Ala Lys Tyr Gly Val Ala Ala Arg
            675                 680                 685

Pro Gly Phe Gly Leu Ser Pro Ile Phe Pro Gly Gly Ala Cys Leu Gly
            690                 695                 700

Lys Ala Cys Gly Arg Lys Arg Lys
705                 710
```

<210> SEQ ID NO 4
<211> LENGTH: 6
<212> TYPE: PRT
<213> ORGANISM: Artificial Sequence
<220> FEATURE:
<223> OTHER INFORMATION: Sequence encoded by forward primer

<400> SEQUENCE: 4

```
Met Ala Gly Leu Thr Ala
 1               5
```

<210> SEQ ID NO 5
<211> LENGTH: 30
<212> TYPE: DNA
<213> ORGANISM: Artificial Sequence
<220> FEATURE:
<223> OTHER INFORMATION: Forward primer

<400> SEQUENCE: 5
ctgctgctgc atatggcggg tctgacggcg          30

<210> SEQ ID NO 6
<211> LENGTH: 16
<212> TYPE: PRT
<213> ORGANISM: Artificial Sequence
<220> FEATURE:
<223> OTHER INFORMATION: Sequence encoded by complement to reverse
      primer

<400> SEQUENCE: 6

```
Ala Cys Gly Arg Lys Arg Lys Gln Lys Leu Ile Ser Glu Glu Asp Leu
 1               5                  10                  15
```

<210> SEQ ID NO 7
<211> LENGTH: 66
<212> TYPE: DNA
<213> ORGANISM: Artificial Sequence
<220> FEATURE:

-continued

<223> OTHER INFORMATION: Reverse primer

<400> SEQUENCE: 7
cgaacaccgg ccttctcttt tgtcttcgac tagtcgctcc tcctggacac tacttctaga    60
cgacga    66

<210> SEQ ID NO 8
<211> LENGTH: 730
<212> TYPE: PRT
<213> ORGANISM: Artificial Sequence
<220> FEATURE:
<223> OTHER INFORMATION: Human elastin-c-myc fusion

<400> SEQUENCE: 8

```
Met Arg Gly Ser His His His His His His Ala Gly Leu Thr Ala Ala
 1               5                  10                  15

Ala Pro Arg Pro Gly Val Leu Leu Leu Leu Ser Ile Leu His Pro
            20                  25                  30

Ser Arg Pro Gly Gly Val Pro Gly Ala Ile Pro Gly Gly Val Pro Gly
        35                  40                  45

Gly Val Phe Tyr Pro Gly Ala Gly Leu Gly Ala Leu Gly Gly Gly Ala
    50                  55                  60

Leu Gly Pro Gly Gly Lys Pro Leu Lys Pro Val Pro Gly Gly Leu Ala
65                  70                  75                  80

Gly Ala Gly Leu Gly Ala Gly Leu Gly Ala Phe Pro Ala Val Thr Phe
                85                  90                  95

Pro Gly Ala Leu Val Pro Gly Gly Val Ala Asp Ala Ala Ala Ala Tyr
            100                 105                 110

Lys Ala Ala Lys Ala Gly Ala Gly Leu Gly Gly Val Pro Gly Val Gly
        115                 120                 125

Gly Leu Gly Val Ser Ala Gly Ala Val Pro Gln Pro Gly Ala Gly
    130                 135                 140

Val Lys Pro Gly Lys Val Pro Gly Val Gly Leu Pro Gly Val Tyr Pro
145                 150                 155                 160

Gly Gly Val Leu Pro Gly Ala Arg Phe Pro Gly Val Gly Val Leu Pro
                165                 170                 175

Gly Val Pro Thr Gly Ala Gly Val Lys Pro Lys Ala Pro Gly Val Gly
            180                 185                 190

Gly Ala Phe Ala Gly Ile Pro Gly Val Gly Pro Phe Gly Gly Pro Gln
        195                 200                 205

Pro Gly Val Pro Leu Gly Tyr Pro Ile Lys Ala Pro Lys Leu Pro Gly
    210                 215                 220

Gly Tyr Gly Leu Pro Tyr Thr Thr Gly Lys Leu Pro Tyr Gly Tyr Gly
225                 230                 235                 240

Pro Gly Gly Val Ala Gly Ala Ala Gly Lys Ala Gly Tyr Pro Thr Gly
                245                 250                 255

Thr Gly Val Gly Pro Gln Ala Ala Ala Ala Ala Ala Lys Ala Ala
            260                 265                 270

Ala Lys Phe Gly Ala Gly Ala Ala Gly Val Leu Pro Gly Val Gly Gly
        275                 280                 285

Ala Gly Val Pro Gly Val Pro Gly Ala Ile Pro Gly Ile Gly Gly Ile
    290                 295                 300

Ala Gly Val Gly Thr Pro Ala Ala Ala Ala Ala Ala Ala Ala Ala
305                 310                 315                 320

Lys Ala Ala Lys Tyr Gly Ala Ala Ala Gly Leu Val Pro Gly Gly Pro
```

```
                    325                 330                 335
Gly Phe Gly Pro Gly Val Val Gly Val Pro Gly Ala Gly Val Pro Gly
                340                 345                 350
Val Gly Val Pro Gly Ala Gly Ile Pro Val Val Pro Gly Ala Gly Ile
            355                 360                 365
Pro Gly Ala Ala Val Pro Gly Val Val Ser Pro Glu Ala Ala Ala Lys
        370                 375                 380
Ala Ala Ala Lys Ala Ala Lys Tyr Gly Ala Arg Pro Gly Val Gly Val
385                 390                 395                 400
Gly Gly Ile Pro Thr Tyr Gly Val Gly Ala Gly Gly Phe Pro Gly Phe
                405                 410                 415
Gly Val Gly Val Gly Gly Ile Pro Gly Val Ala Gly Val Pro Gly Val
                420                 425                 430
Gly Gly Val Pro Gly Val Gly Val Pro Gly Val Gly Ile Ser Pro
            435                 440                 445
Glu Ala Gln Ala Ala Ala Ala Lys Ala Ala Lys Tyr Gly Val Gly
    450                 455                 460
Thr Pro Ala Ala Ala Ala Lys Ala Ala Lys Ala Ala Gln Phe
465                 470                 475                 480
Ala Leu Leu Asn Leu Ala Gly Leu Val Pro Gly Val Gly Val Ala Pro
                485                 490                 495
Gly Val Gly Val Ala Pro Gly Val Gly Val Ala Pro Gly Val Gly Leu
                500                 505                 510
Ala Pro Gly Val Gly Val Ala Pro Gly Val Gly Val Ala Pro Gly Val
            515                 520                 525
Gly Val Ala Pro Gly Ile Gly Pro Gly Val Ala Ala Ala Ala Lys
            530                 535                 540
Ser Ala Ala Lys Val Ala Ala Lys Ala Gln Leu Arg Ala Ala Ala Gly
545                 550                 555                 560
Leu Gly Ala Gly Ile Pro Gly Leu Gly Val Gly Val Gly Val Pro Gly
                565                 570                 575
Leu Gly Val Gly Ala Gly Val Pro Gly Leu Gly Val Gly Ala Gly Val
                580                 585                 590
Pro Gly Phe Gly Ala Val Pro Gly Ala Leu Ala Ala Ala Lys Ala Ala
            595                 600                 605
Lys Tyr Gly Ala Ala Val Pro Gly Val Leu Gly Gly Leu Gly Ala Leu
        610                 615                 620
Gly Gly Val Gly Ile Pro Gly Gly Val Val Gly Ala Gly Pro Ala Ala
625                 630                 635                 640
Ala Ala Ala Ala Ala Lys Ala Ala Lys Ala Ala Gln Phe Gly Leu
                645                 650                 655
Val Gly Ala Ala Gly Leu Gly Gly Leu Gly Val Gly Gly Leu Gly Val
            660                 665                 670
Pro Gly Val Gly Gly Leu Gly Gly Ile Pro Pro Ala Ala Ala Lys
            675                 680                 685
Ala Ala Lys Tyr Gly Val Ala Ala Arg Pro Gly Phe Gly Leu Ser Pro
    690                 695                 700
Ile Phe Pro Gly Gly Ala Cys Leu Gly Lys Ala Cys Gly Arg Lys Arg
705                 710                 715                 720
Lys Gln Lys Leu Ile Ser Glu Glu Asp Leu
                725                 730
```